(12) United States Patent
Al-Babili

(10) Patent No.: US 10,888,090 B2
(45) Date of Patent: Jan. 12, 2021

(54) PLANT GROWTH PROMOTERS AND METHODS OF USING THEM

(71) Applicant: KING ABDULLAH UNIVERSITY OF SCIENCE AND TECHNOLOGY, Thuwal (SA)

(72) Inventor: Salim Al-Babili, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 0 days.

(21) Appl. No.: 15/738,928

(22) PCT Filed: Jun. 28, 2016

(86) PCT No.: PCT/IB2016/001058
§ 371 (c)(1),
(2) Date: Dec. 21, 2017

(87) PCT Pub. No.: WO2017/001927
PCT Pub. Date: Jan. 5, 2017

(65) Prior Publication Data
US 2018/0184651 A1 Jul. 5, 2018

Related U.S. Application Data

(60) Provisional application No. 62/186,705, filed on Jun. 30, 2015.

(51) Int. Cl.
*A01N 35/02* (2006.01)
*A01N 49/00* (2006.01)
*A01N 37/42* (2006.01)
*C07C 49/242* (2006.01)
*C07C 59/90* (2006.01)
*C07C 62/38* (2006.01)

(52) U.S. Cl.
CPC ............ *A01N 35/02* (2013.01); *A01N 37/42* (2013.01); *A01N 49/00* (2013.01); *C07C 49/242* (2013.01); *C07C 59/90* (2013.01); *C07C 62/38* (2013.01); *C07C 2601/16* (2017.05)

(58) Field of Classification Search
None
See application file for complete search history.

(56) References Cited

U.S. PATENT DOCUMENTS

| | | | |
|---|---|---|---|
| 5,837,653 | A | 11/1998 | Finch |
| 7,132,458 | B2 | 11/2006 | Burton et al. |
| 7,858,828 | B2 | 12/2010 | Khachik et al. |
| 8,211,461 | B2 | 7/2012 | Burton et al. |
| 8,980,795 | B2 | 3/2015 | Al-Babili et al. |
| 2009/0069417 | A1 | 3/2009 | Sharoni et al. |
| 2009/0264681 | A1 | 10/2009 | Khachik et al. |
| 2009/0303222 | A1 | 12/2009 | Burton et al. |
| 2010/0022562 | A1* | 1/2010 | Liu ............ A01H 3/04 514/263.4 |
| 2010/0048516 | A1* | 2/2010 | Baur ............ A01N 57/12 514/143 |
| 2010/0179061 | A1 | 7/2010 | Saito |
| 2010/0331189 | A1 | 12/2010 | Fukuzawa et al. |
| 2011/0088128 | A1 | 4/2011 | De Seixas Boavida Ferreira et al. |
| 2012/0172623 | A1 | 7/2012 | Yokoyama |
| 2012/0295788 | A1* | 11/2012 | Stoller ............ A01N 43/90 504/124 |
| 2014/0106967 | A1* | 4/2014 | Ozga ............ C05F 11/10 504/103 |
| 2015/0011392 | A1 | 1/2015 | Haas et al. |
| 2015/0087508 | A1 | 3/2015 | Villedieu-Percheron et al. |

FOREIGN PATENT DOCUMENTS

| | | |
|---|---|---|
| EP | 0371882 | 6/1990 |
| EP | 0887017 | 12/1998 |

OTHER PUBLICATIONS

D.A. Williams et al., "Drug Design and Relationship of Functional Groups to Pharmacologic Activity," Foyes Principles of Medicinal Chemistry, 5th Edition, Copyright 2002, p. 37-67.*
T. Koyanagi et al., "Bioisosterism in Agrochemicals," Synthesis and Chemistry of Agrochemicals IV, Chapter 2, Copyright 1995 American Chemical Society, pp. 15-24.*
International Search Report and Written Opinion received in connection with International Application No. PCT/IB2016/001058; dated Dec. 20, 2016.
Alder A, et al., 2008. Carotenoid oxygenases involved in plant branching catalyse a highly specific conserved apocarotenoid cleavage reaction. The Biochemical journal 416:289-96.
Alder A, et al., 2012. The path from beta-carotene to carlactone, a strigolactone-like plant hormone. Science 335:1348-51.
Anslyn, Dougherty, Modern Physical Organic Chemistry, 2006, Chapter 17 on Organic Electronic Materials.
Auldridge ME, et al., 2006. Plant carotenoid cleavage oxygenases and their apocarotenoid products. Current opinion in plant biology 9:315-21.

(Continued)

*Primary Examiner* — Monica A Shin
(74) *Attorney, Agent, or Firm* — Pabst Patent Group LLP

(57) ABSTRACT

New plant growth regulators, including compounds and compositions, and methods of use including for promoting root growth. The compounds are carotenoid oxidation products, and a preferred example is 3-OH-β-apo-13-Carotenone. A method comprising promoting the growth of at least one plant with use of an effective amount of at least one composition comprising an effective amount of at least one compound which is represented by A-B-C, wherein B is a bivalent polyene moiety, A is a monovalent moiety linked to B by a six-membered carbon ring, wherein the ring has at least one substituent linked to the ring by an oxygen atom, and C is a monovalent moiety linked to B by a carbonyl group. Synergistic effects can be used with combinations of compounds.

13 Claims, 18 Drawing Sheets

(56) References Cited

OTHER PUBLICATIONS

Avendano-Vazquez AO, et al., 2014. An Uncharacterized Apocarotenoid-Derived Signal Generated in zeta-Carotene Desaturase Mutants Regulates Leaf Development and the Expression of Chloroplast and Nuclear Genes in *Arabidopsis*. The Plant cell 26:2524-37.

Bellini C, et al., 2014. Adventitious roots and lateral roots: similarities and differences. Annual review of plant biology 65:639-66.

DellaPenna D, et al., 2006. Vitamin Synthesis in Plants: Tocopherols and Carotenoids. Annu. Rev. Plant Biol. 57:711-38.

Etoh et al., auto-Oxidation Products of Astaxanthin J. of Oleo Science, vol. 61 2012, pp. 17-21.

Frusciante S, et al., 2014. Novel carotenoid cleavage dioxygenase catalyzes the first dedicated step in saffron crocin biosynthesis. Proceedings of the National Academy of Sciences of the United States of America 111.

Hayakawa et al., "Reaction of Astaxanthin with Peroxynitrite", Biosci. Biotechnol. Biochem, vol. 72, 2008, pp. 2716-2722.

Kachanovsky DE, et al., 2012. Epistasis in tomato color mutations involves regulation of phytoene synthase 1 expression by cis-carotenoids. *Proc Natl Acad Sci U S A* 109:19021-6.

Manual on Development and Use of FAO Specifications for Plant Protection Products, 5th Edition, 1999.

Maoka et al., "Isolation of a series of apocarotenoids frm the fruits of the red paprika *Capsicum annuum* L.", J. Agric. Food Chem. 2001, 49, 1601-1606.

Medina HR, et al., 2011. Cleavage oxygenases for the biosynthesis of trisporoids and other apocarotenoids in Phycomyces. *Molecular microbiology* 82:199-208.

Moise AR, et al., 2014. Mechanistic aspects of carotenoid biosynthesis. *Chemical reviews* 114:164-93.

Moise AR, et al., 2005. Related enzymes solve evolutionarily recurrent problems in the metabolism of carotenoids. *Trends in plant science* 10:178-86.

Oritani et al (1970), "Studies on Abscisic Acid. Part V. The Epoxidation Products of Methyl DeHydro-ß-ionylideneacetates", Agricultural and Biological Chemistry, vol. 34(12), pp. 1821-1825.

Oritani et al (1972), "Studies on Abscisic Acid Part VI. Syntheses of Hydroxy-ionylideneacetic Acids", Agricultural and Biological Chemistry, vol. 36(3), pp. 362-369.

Peret B, et al., 2011. Root developmental adaptation to phosphate starvation: better safe than sorry. *Trends in plant science* 16:442-50.

Pijut, PM, et al., 2011. Promotion of adventitious Root formation of Difficult-to-Root hardwood tree species. Horticultural reviews 38:213-251.

Ramel F, et al., Triantaphylides C, Havaux M. 2012. Carotenoid oxidation products are stress signals that mediate gene responses to singlet oxygen in plants. Proc Natl Acad Sci U S A 109:5535-40.

Rogers ED, et al., 2014. Regulation of plant root system architecture: implications for crop advancement. Current opinion in biotechnology 32C:93-8.

Scherzinger D, et al., "The Mycobacterium tuberculosis ORF Rv0654 encodes a carotenoid oxygenase mediating central and excentric cleavage of conventional and aromatic carotenoids", FEBS Journal, vol. 277 (2010) 4662-4673.

Schlicht M, et al., 2008. "D'orenone blocks polarized tip growth of root hairs by interfering with the PIN2-mediated auxin transport network in the root apex". The Plant journal : for cell and molecular biology 55:709-17.

Schwartz SH. 1997. Specific Oxidative Cleavage of Carotenoids by VP14 of Maize. Science 276:1872-4.

Srivastava, Plant Growth and Development: Hormones and Environment, 2002 (Table of Contents).

Van Norman JM, et al., 2014. Periodic root branching in *Arabidopsis* requires synthesis of an uncharacterized carotenoid derivative. Proc Natl Acad Sci U S A 111:E1300-9.

Walter MH, et al., 2010. Apocarotenoids: hormones, mycorrhizal metabolites and aroma volatiles. Planta 232:1-17.

Walter MH, et al., 2011. Carotenoids and their cleavage products: biosynthesis and functions. Nat Prod Rep 28:663-92.

\* cited by examiner

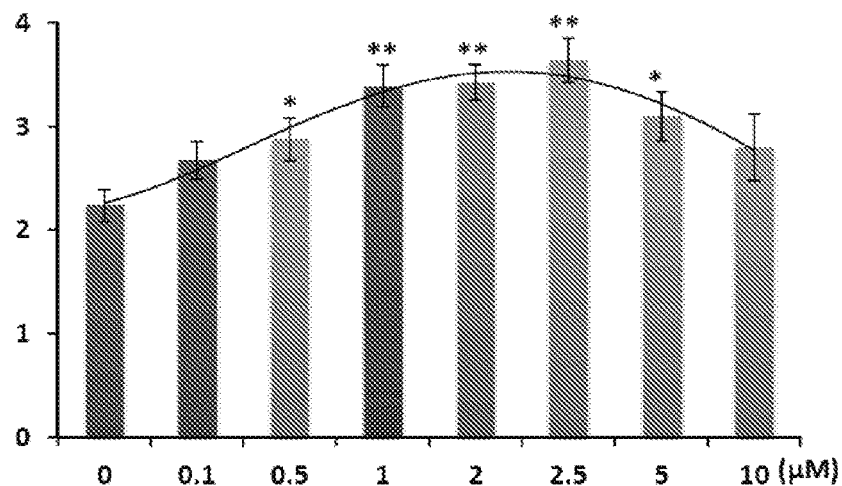
- Media : ½ MS with 0.5% Sucrose
- Growth condition : 4 days in dark for germination & hypocotyl elongation 10 days in 16 light/8 dark, 22°C for all period
- ** : significantly different at the p=0.01 level (Student T-test)
FIG. 12A
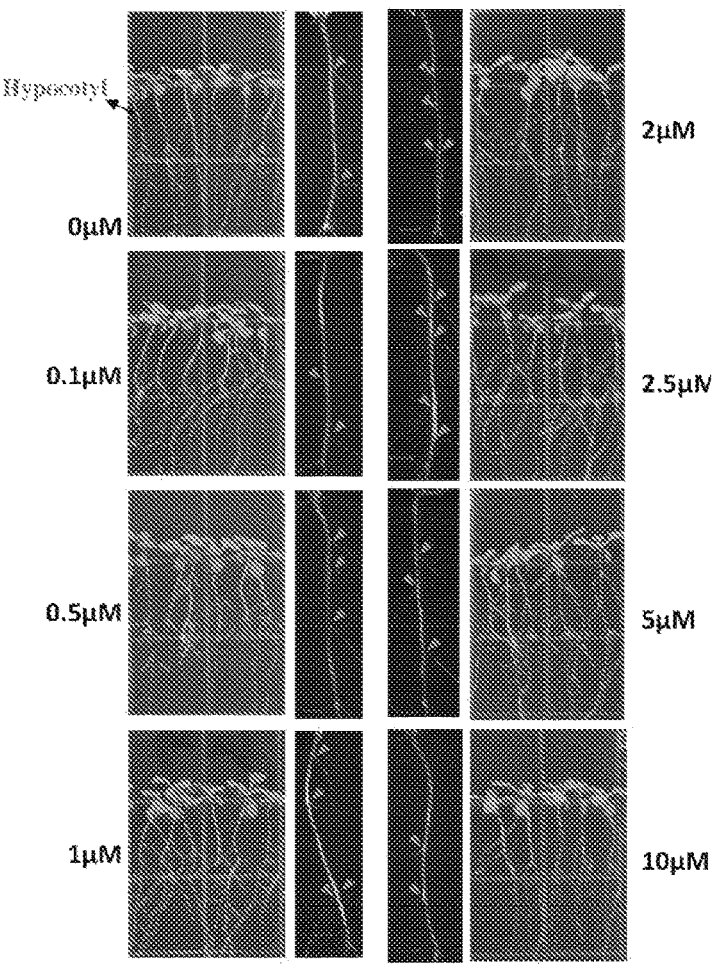

PLANT GROWTH PROMOTERS AND METHODS OF USING THEM

CROSS REFERENCE TO RELATED APPLICATION

This is a national stage application of International Application No. PCT/IB2016/001058, filed internationally on Jun. 28, 2016, which claims priority to U.S. Provisional Application Ser. No. 62/186,705, filed on Jun. 30, 2015, both of which are incorporated by reference herein in their entireties.

BACKGROUND

Carotenoids are widely distributed isoprenoid pigments characterized by their bright yellow to red colors (for examples and biosynthesis, see FIGS. 1 and 2; for review see, references 6 and 10 from the list of references provided below). Carotenoids differ in the number of conjugated double bonds, the presence and type of cyclic end groups, and oxygen-containing functional group. Carotenoids are known as essential components of the photosynthetic apparat. In addition, they serve as a platform that is used by many organisms to generate bioactive compounds acting as hormones or chemical signals. Outstanding examples for such compounds are retinol (vitamin A), retinoic acid, and retinal, which are essential for vision and development in vertebrates, and the plant hormones abscisic acid and strigolactones, which regulate different aspects of plant growth, development and adaptation to environment (See references 11, 19, and 20; for structures, see FIG. 3).

It is possible that there are still unidentified plant carotenoid-derived signaling molecules and growth regulators, as indicated by different plant mutants and by studies on inhibitors of carotenoid biosynthesis. Examples of such compounds might be involved in the regulation of other processes in plants, such as lateral root formation (18), early chloroplast and leaf development (4), and carotenoid biosynthesis (8).

The first step in the formation of carotenoid-derived compounds is catalyzed by a ubiquitous family of enzymes, the carotenoid cleavage oxygenases (CCOs) that mediate the oxidative cleavage of a double bond in the carotenoid back-bone, leading to carbonyl products generally called apocarotenoids (20). In plants, CCOs are divided into two groups, the nine-cis-epoxy-carotenoid dioxygenases (NCEDs) and the carotenoid cleavage dioxygenaeses (CCDs) (3; 20). NCEDs are involved in ABA biosynthesis (FIG. 4), providing the ABA precursor xanthoxin by cleaving the C10-C11' double bond in 9-cis-configured xanthophylls (epoxy-carotenoids), such as 9-cis-violaxanthin or 9'-cis-violaxanthin (17, 20). The second group is the carotenoid cleavage dioxygenaeses (CCD) that encompasses enzymes with different substrate-, stereo- and double bond specificities. There are four major groups of plant CCDs: CCD1, CCD4, CCD7, and CCD8. CCD1 enzymes produce various carotenoid derived volatiles such as β-ionone and geranial. CCD4 enzyme activity is a negative regulator of carotenoid content in different tissue and is supposed to be involved in heat stress response. The two types, CCD7 and CCD8 catalyze two distinct steps in the biosynthesis of strigolactones (2) (FIG. 5). In contrast to CCD1, CCD4 and CCD7, plant CCD8 enzymes do not cleave intact carotenoids, such as β-carotene, but only already cleaved carotenoids (apocarotenoids) (1). A further unique feature of this enzyme is its capability to form two totally different products, i.e. carlactone or β-apo-13-carotenone, depending on the cis/trans-isomerism state of the substrate β-apo-10'-carotenal (FIG. 5) (2). The *Arabidopsis* genome encodes 5 NCEDs and 4 CCDs belonging to the above mentioned 4 groups (20). However, other plants have additional types of CCOs enzymes (7).

U.S. Pat. No. 7,858,828 describes in FIG. 6 a C18-ketone compound 28 illustrated below:

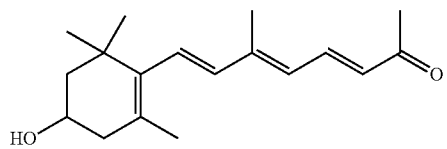

called (3-R)-3-Hydroxy-β-apo-β-caroten-13-one. The compound is obtained by oxidative cleavage of a precursor compound. The '828 reference does not describe specific applications for such compounds but merely comments briefly and generally about diet, AMD, and blindness. This compound is also briefly noted in Scherzinger et al., *FEBS Journal* 277 (2010) 4662-4673 (Ref. 15 below) in a study of carotenoid cleavage reactions.

The reference Schlicht et al. (*The Plant Journal*, 2008, 55, 709-717; reference 16 below; see also reference 9) describes the following compound called "D'orenone:

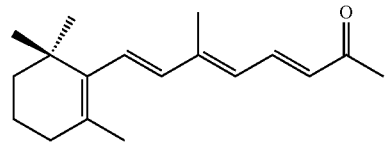

which is said to block polarized tip growth of root hairs.

Despite these advances in understanding of natural processes, a need yet exists to develop better compounds, compositions, and methods for commercial plant growth regulation and promotion. This includes both for the aerial part of the plant as well as plant roots. However, the promotion of root growth is particularly important. Better active ingredients are needed.

SUMMARY

Embodiments described herein include compounds, compositions, and methods of making and using such compounds and compositions. Kits can also be prepared including, for example, the compounds or compositions, properly packaged, along with instructions for carrying out the methods of use.

For example, a first aspect provides for a method comprising promoting the growth of at least one plant with use of an effective amount of at least one composition comprising at least one compound which is represented by A-B-C, wherein B is a bivalent polyene moiety, A is a monovalent moiety linked to B by a six-membered carbon ring, wherein the ring has at least one substituent linked to the ring by an oxygen atom, and C is a monovalent moiety linked to B by a carbonyl group.

A second aspect provides for a composition comprising (i) at least one compound which is represented by A-B-C, wherein B is a bivalent polyene moiety, A is a monovalent moiety linked to B by a six-membered carbon ring, wherein the ring has at least one substituent linked to the ring by an oxygen atom, and C is a monovalent moiety linked to B by a carbonyl group; and (ii) at least one compound which facilitates delivery of the compound for promoting the growth of at least one plant.

In some method and composition embodiments, the bivalent polyene moiety B is a $C_4$-$C_{20}$ hydrocarbon moiety with no heteroatoms.

In some method and composition embodiments, the bivalent polyene moiety B has three conjugated double bonds.

In some method and composition embodiments, the double bonds of bivalent polyene moiety B are in an all trans configuration.

In some method and composition embodiments, B is represented by:

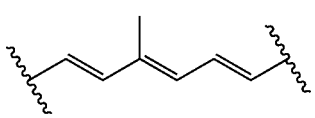

In some method and composition embodiments, the six-membered ring is a phenyl ring, a cyclohexane ring, a cyclohexadiene ring, or a cyclohexene ring.

In some method and composition embodiments, the six-membered ring is an unsaturated ring.

In some method and composition embodiments, the monovalent moiety A consists of only one cyclohexene ring.

In some method and composition embodiments, the monovalent moiety A comprises a cyclohexene ring, and the cyclohexene ring has a double bond in conjugation with a double bond of the polyene moiety B.

In some method and composition embodiments, the monovalent moiety A, the substituent is a hydroxyl, ketone, epoxy, alkoxy, or polyether moiety.

In some method and composition embodiments, the monovalent moiety A is represented by:

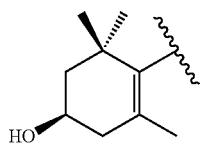

In some method and composition embodiments, the monovalent moiety C linked to B by a carbonyl moiety is represented by —C(O)—R, wherein R is an alkyl group or a carboxylic acid group.

In some method and composition embodiments, C is represented by:

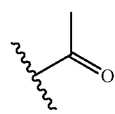

In some method and composition embodiments, the compound is represented by structure Z:

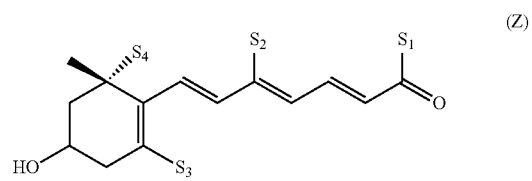

wherein $S_1$ is an alkyl or a carboxylic acid group; wherein $S_2$ is an alkyl, carboxylic acid, or —$CH_2OH$ group; wherein $S_3$ is an alkyl, a carboxylic acid, or a —$CH_2OH$ group; and wherein $S_4$ is an alkyl, carboxylic acid, or —$CH_2OH$ group, wherein optionally $S_1$, $S_2$, $S_3$, and $S_4$ are each methyl.

In some method and composition embodiments, the compound is 3-OH-β-apo-13-carotenone.

In some method and composition embodiments, the compound is one of the following structures (I)-(VIII):

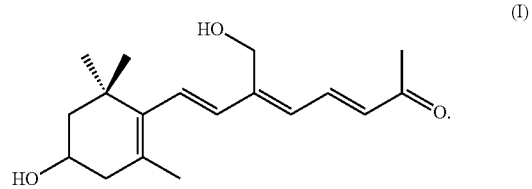

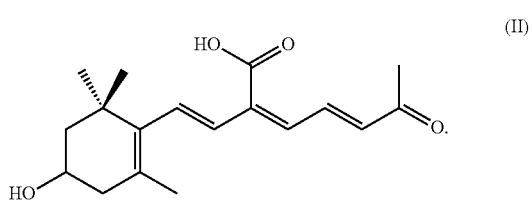

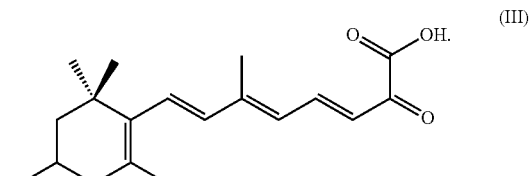

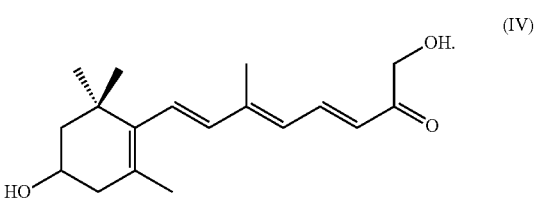

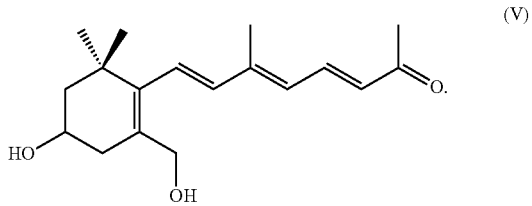

-continued

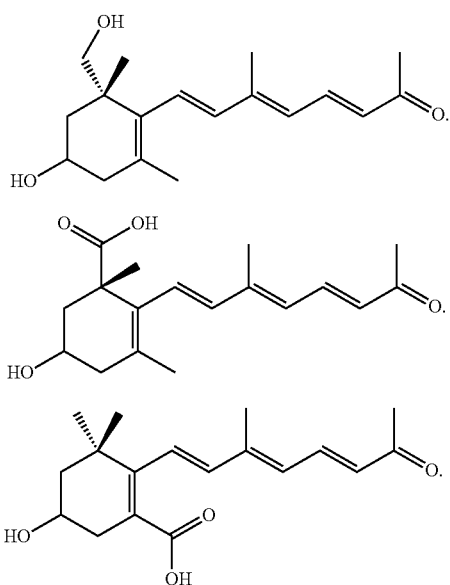

In some method and composition embodiments, the compound is a first compound, and the composition further comprises at least one second compound different from the first and which also is a plant growth regulator, wherein optionally the second compound is auxin, cytokinin, gibberlin, or ethylene.

In some method and composition embodiments, the composition further comprises at least one aqueous solvent system.

In some method and composition embodiments, the composition further comprises at least one delivery compound which is different from the compound which is represented by A-B-C and which facilitates delivery of the compound which is represented by A-B-C for promoting the growth of at least one plant.

In some method and composition embodiments, the plant is a monocotyledon, a dicotyledon, a gymnosperm, a cereal, or an algae.

Another embodiment is a plant propagation material treated with a composition as described and/or claimed herein.

A third aspect is a compound represented by structure Z:

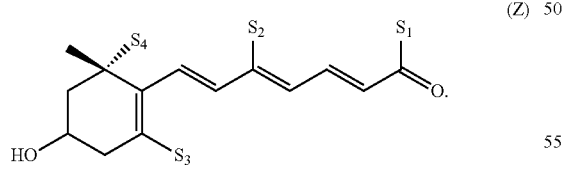

wherein $S_1$ can be an alkyl or a carboxylic acid group; wherein $S_2$ can be an alkyl, carboxylic acid, or —$CH_2OH$ group; wherein $S_3$ can be an alkyl, a carboxylic acid, or a —$CH_2OH$ group; and wherein $S_4$ can be an alkyl, carboxylic acid, or —$CH_2OH$ group. The alkyl group can be, for example, a $C_1$ to $C_4$ alkyl. In one embodiment, $S_1$, $S_2$, $S_3$, and $S_4$ are each methyl. In another embodiment, $S_1$, $S_2$, $S_3$, and $S_4$ are each not methyl. In structure Z, the —OH moiety stereochemically can be above or below the cyclohexene ring.

A fourth aspect is a compound represented by one of the following structures (I)-(VIII):

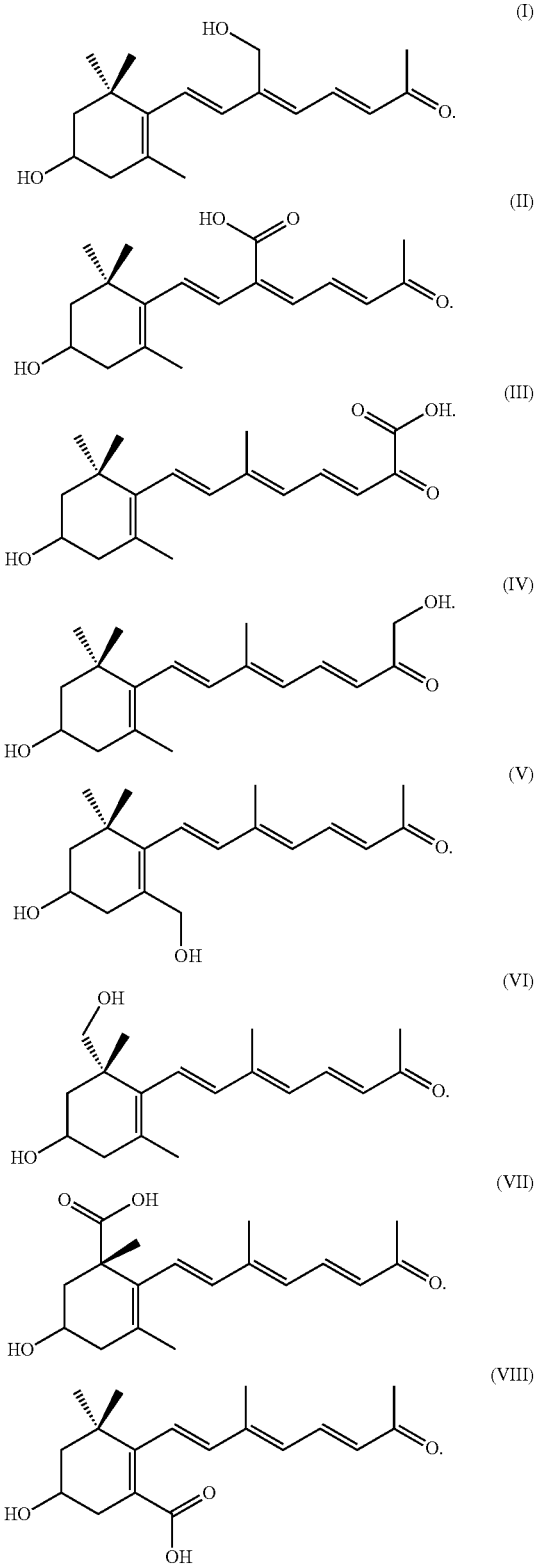

Other embodiments include a purified form of the compounds as described and/or claimed herein.

An advantage for at least some embodiments is improved plant root growth. Plant growth can be improved, and biomass can be enhanced. In addition, combinations of compounds can be used, and synergistic improvements can be observed with use of multiple compounds. An additional advantage for at least some embodiments includes use and potential use for a wide spectrum of plants. An additional advantage for at least some embodiments is the active ingredient is a natural compound rather than a synthetic compound. This can contribute to limited environmental impact and regulatory burden and reduced plant toxicity.

BRIEF DESCRIPTION OF THE DRAWINGS

FIG. 10: 3-OH-β-apo-13-Carotenone treatment increases the number of crown roots in rice. Seeds of cultivar 'Dongjin' were pre-germinated in water for 2 days followed by transfer to filter papers placed in petri dishes containing half-strength liquid Murashige and Skoog (MS) medium. The cultures were incubated at 24° C. for one week. Thereafter, the seedlings were grown hydroponically in half-strength modified Hoagland nutrient solution containing different concentrations of 3-OH-β-apo-13-carotenone for 2 weeks in the greenhouse. The medium was changed twice a week, data were recorded 2 weeks after treatment.

IAA: Indol acetic acid (positive control) applied at 1 µM concentration.

Apo: β-apo-13-carotenone. Concentrations applied are shown in µM.

Figure 11:
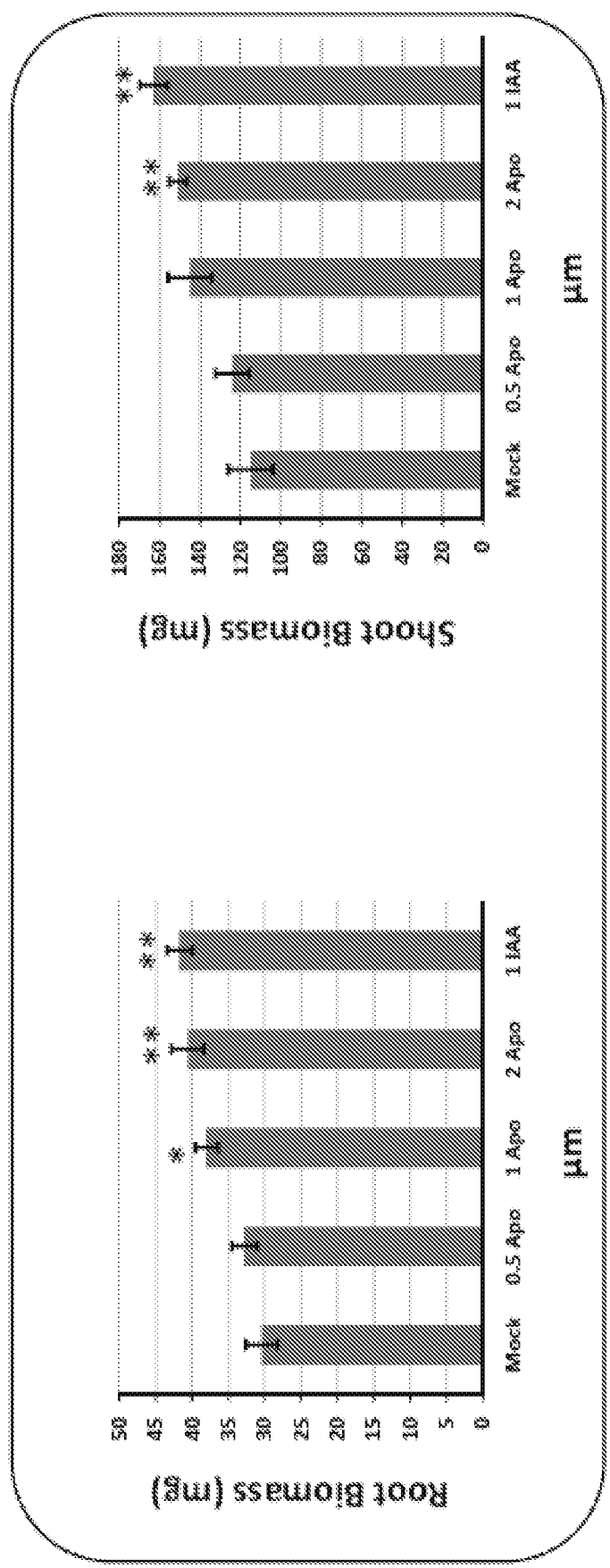

FIG. 11: Root and shoot biomass of rice seedlings treated with 3-OH-β-apo-13-Carotenone. One week-old seedlings of cultivar 'Dongjin' were grown hydroponically in half-strength modified Hoagland nutrient solution containing different concentrations of 3-OH-β-apo-13-Carotenone for two weeks in the greenhouse. The medium was changed twice a week. After two weeks, roots and shoots were collected separately and dried in an incubator at 80° C. for 3 days. Dried samples were weighed using a Mettler Toledo balance. Each value represents the mean of 10 seedlings. Error bar indicates standard error. Asterisks denote significant difference from the mock treatment by student t-test (* P<0.05; ** P<0.01). IAA: Indol acetic acid (positive control). Apo: b-apo-13-Carotenone. Concentrations applied are shown in µM.

Figure 12B:
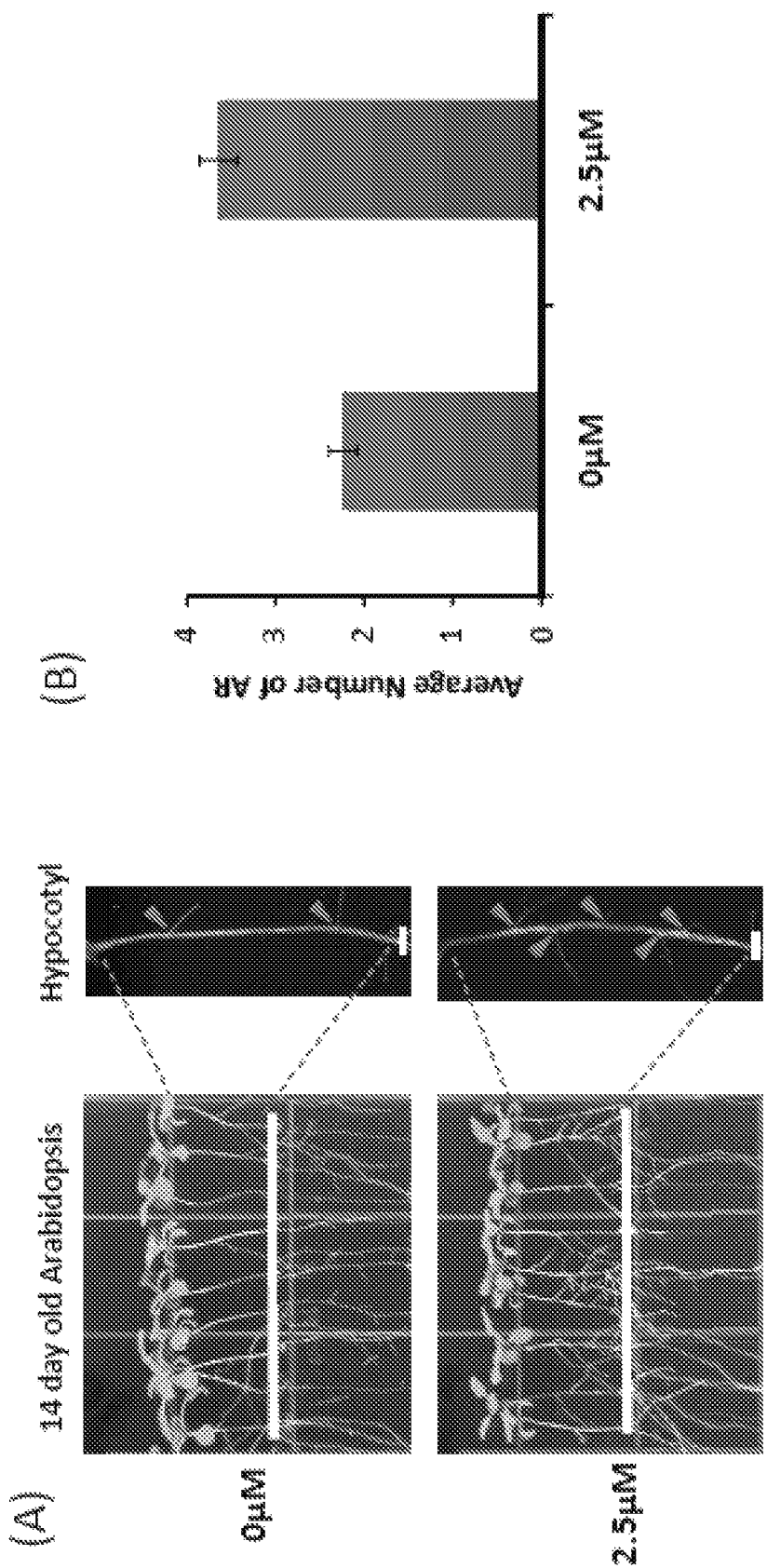

FIG. 12A: 3-OH-β-apo-13-Carotenone treatment increases the number of hypocotyl-derived adventitious roots in a concentration-dependent manner (14 days old plants). For a better resolution, see FIG. 12B.

FIG. 12B: 3-OH-β-apo-13-Carotenone treatment increases the number of hypocotyl-derived adventitious roots. (A) 4-day-old *Arabidopsis* (col-0) seedlings were transferred to 3-OH-β-apo-13-Carotenone containing plates at the indicated concentrations and grown for 10 days. Red arrows indicate adventitious roots on hypocotyl (B) Average number of adventitious roots. Seeds were germinated on 1 MS medium with 0.5% sucrose (pH 5.7) and grown for 4 days in the dark. Error bars represent means±S.E. Asterisks indicate significant differences as calculated using a standard Student's t-test (*P<0.005, ** <0.001).

Figure 13:
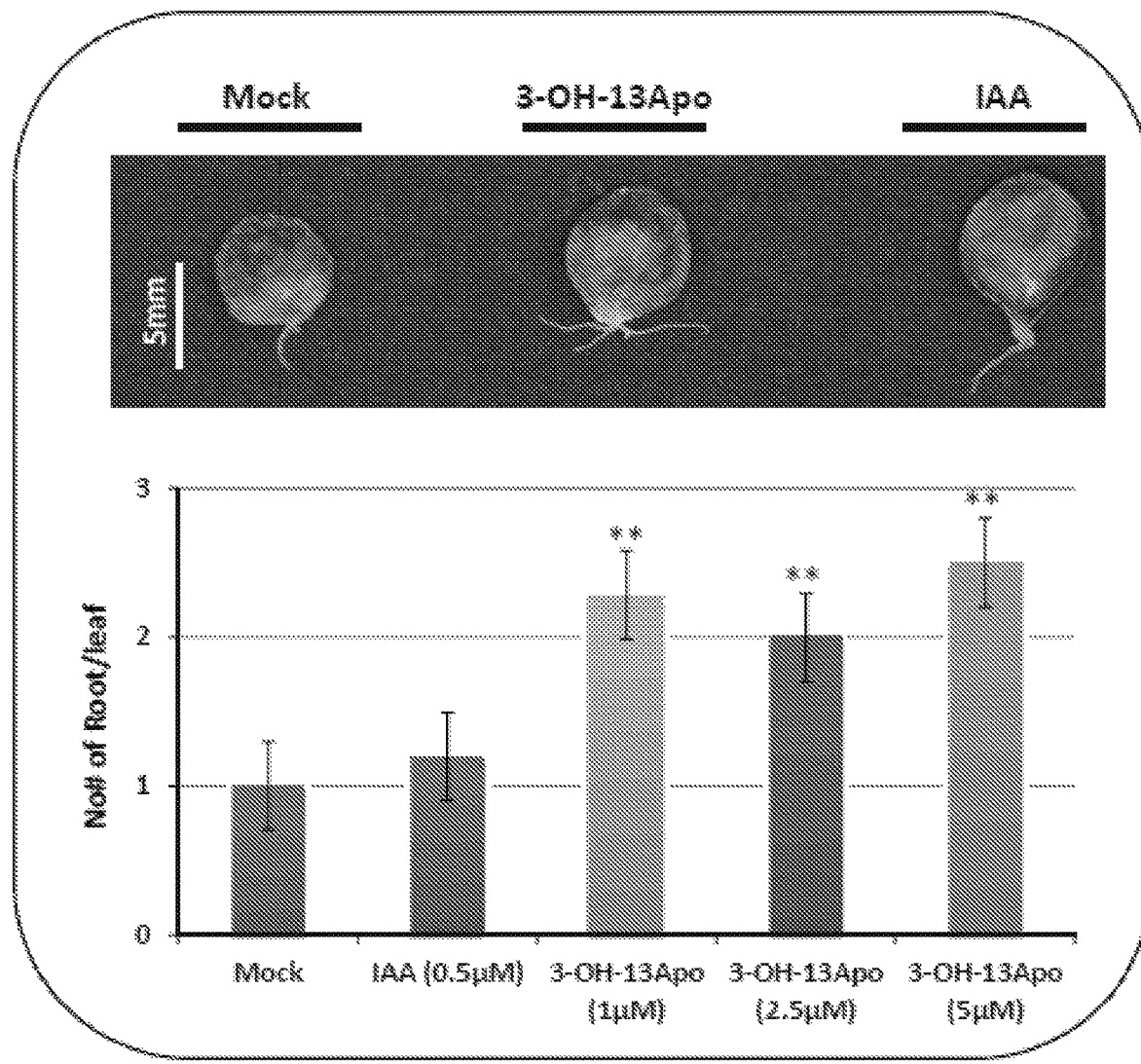

FIG. 13: 3-OH-β-apo-13-Carotenone treatment increases the number of leaf-derived adventitious roots (Leaf explants of 12-day-old seedlings). IAA: Indol acetic acid (positive control)

Figure 14:
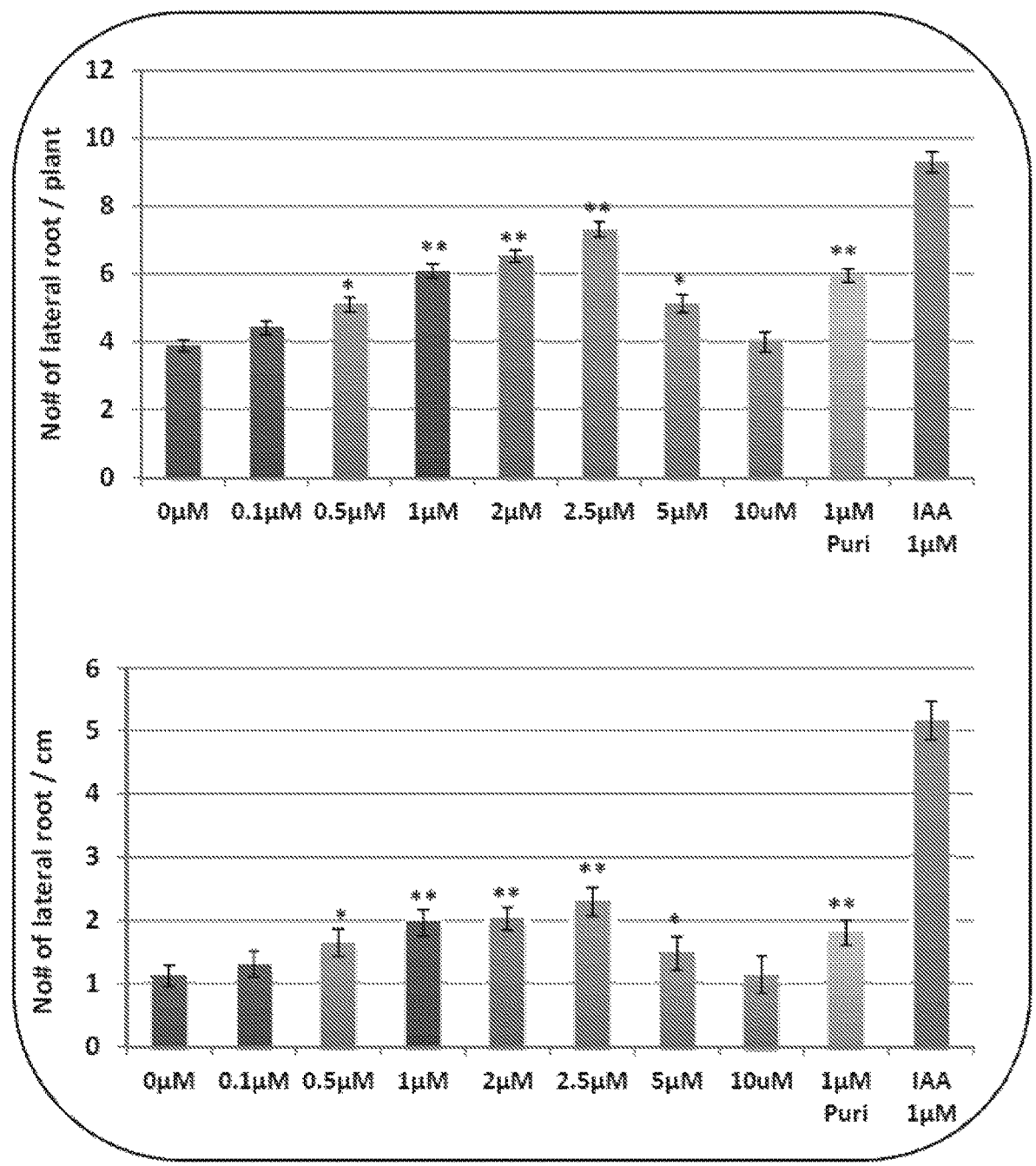

FIG. 14: 3-OH-β-apo-13-Carotenone treatment of *Arabidopsis* increases the number of lateral roots in a concentration-dependent manner (14 days old plants). 0-5 µM corresponds to different concentrations of synthetic 3-OH-β-apo-13-Carotenone. Puri corresponds to synthetic 3-OH-β-apo-13-Carotenone after HPLC purification. IAA: indol acetic acid (positive control)

Figure 15:
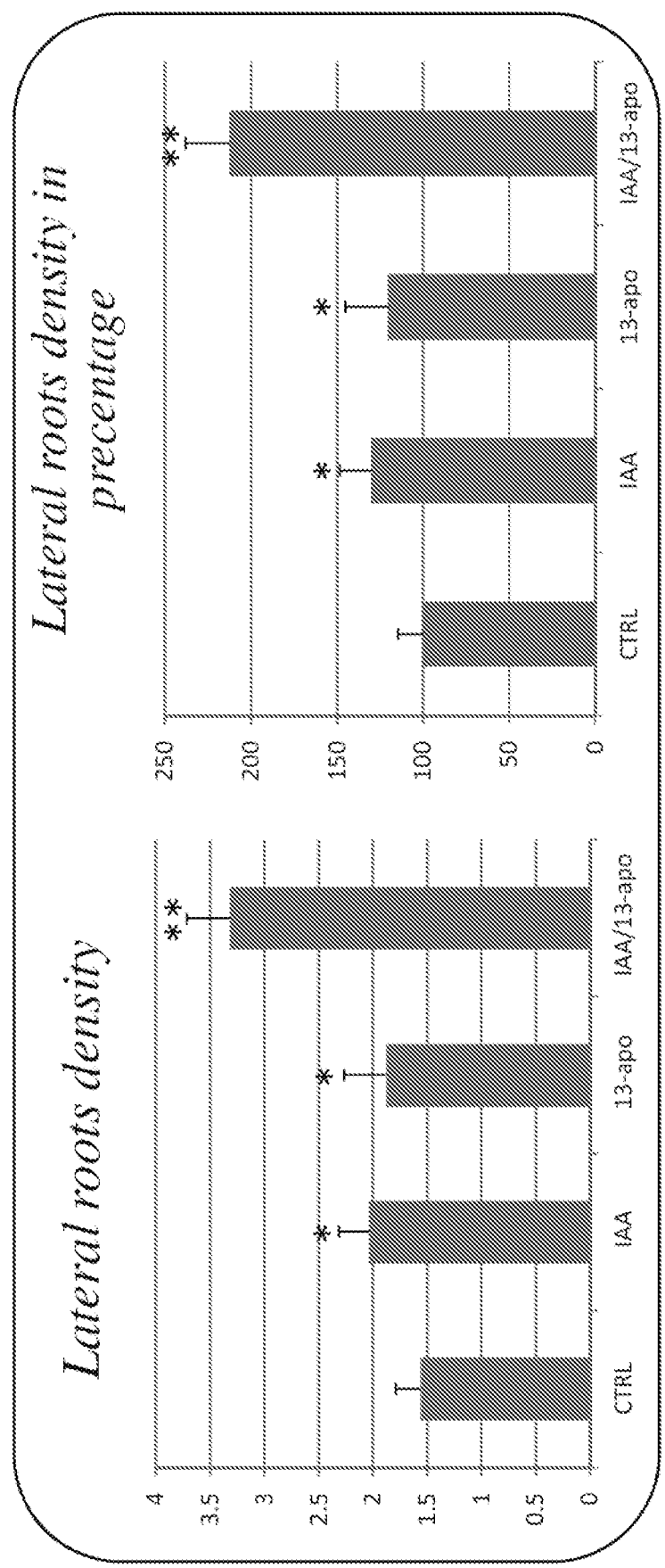

FIG. 15: Combined 3-OH-β-apo-13-Carotenone and auxin treatment of *Arabidopsis* has a synergetic effect on lateral root density. 3-OH-β-apo-13-carotenone and auxin (indole-3-acetic acid) were applied at 2.5 µM and 100 nM, concentrations, respectively. *Arabidopsis* (Col-0) seeds were germinated in/MS-plates (with 0.5% sucrose) containing individual and both compounds together and grown in 16 light/8 dark period, 22° C. for 9 days. Graph represents both actual density and in percentage. *P<0.05; Student's t test; **P<0.05; Student's t test.

Figure 16:
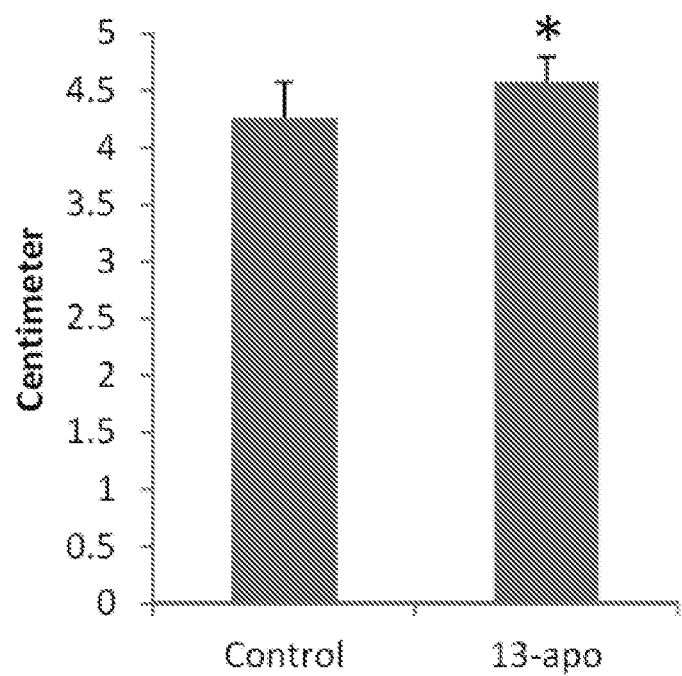

FIG. 16: 3-OH-β-apo-13-Carotenone treatment of *Arabidopsis* increases the length of primary root. *Arabidopsis* (Col-0) seeds were germinated on/MS-plates (with 0.5% sucrose) containing 3-OH-β-apo-13-carotenone and grown in 16 light/8 dark period, 22° C. for 9 days. *P<0.05; Student's t-test; **P<0.05; Student's t test. 3-OH-β-apo-13-carotenone was applied at 2.5 µM concentration.

DETAILED DESCRIPTION

Introduction

Additional details about the different embodiments described, summarized, and claimed herein are provided. Methods of uses, compounds, and compositions are described.

Nomenclature for carotenoid compounds is generally known in the art.

Plant growth promotion is generally known in the art. See, for example, US Patent Publication Nos. 2010/0179061; 2012/0172623; 2010/0331189; 2011/0088128. See also, for example, L. M. Srivastava, *Plant Growth and Development: Hormones and Environment*, 2002. See also, for example, U.S. Pat. No. 8,980,795.

In this application, chemical formulae are shown. The formulae generally describe and encompass each and every stereo configuration, whether enantiomers or diastereomers, unless otherwise specified.

Method of Use

One embodiment provides for a method comprising promoting the growth of at least one plant with use of an effective amount of at least one composition comprising an effective amount of at least one compound which is represented by A-B-C, wherein B is a bivalent polyene moiety, A is a monovalent moiety linked to B by a cyclohexene or cyclohexane ring, wherein the ring has at least one substituent linked to the ring by an oxygen atom, and C is a monovalent moiety linked to B by a carbonyl group.

The compounds and compositions which are the subject of the method of use are described further.

Compounds

In one embodiment, a compound, which can be made and used by methods described herein, can be represented by A-B-C, wherein B is a bivalent polyene moiety, A is a monovalent moiety linked to B by a six-membered carbon ring, wherein the ring has at least one substituent linked to the ring by an oxygen atom, and C is a monovalent moiety linked to B by a carbonyl group.

Polyene moieties, whether oligomeric or polymeric, are generally known in the art. See, for example, reference 10; or Anslyn, Dougherty, *Modern Physical Organic Chemistry*, 2006, Chapter 17 on Organic Electronic Materials, for example. Polyenes can comprise conjugated ethylenically unsaturated double bonds as in oligomeric or polymeric polyacetylene moieties. The polyenes can be extensively or fully conjugated. The polyene chain can be understood to have a backbone with optional substituents, replacing hydrogen. The polyene chain can be unsubstituted or substituted. For example, an alkyl group such as a $C_1$-$C_6$ alkyl group such as a methyl or ethyl can replace a hydrogen. In another example, and alkoxy group such as methoxy or ethoxy can replace hydrogen. The polyene moiety can be an all hydrocarbon chain whether substituted or unsubstituted.

In one embodiment, the bivalent polyene moiety B is a hydrocarbon moiety with no heteroatoms. In another embodiment, the bivalent polyene moiety B is a $C_4$-$C_{20}$ hydrocarbon moiety with no heteroatoms. In another embodiment, the bivalent polyene moiety B is a $C_5$-$C_{10}$ hydrocarbon moiety with no heteroatoms.

In one embodiment, the bivalent polyene moiety B can be represented by the bivalent moiety —[(CHR$_a$═CHR$_b$) x]— wherein x is the number of double bonds in the polyene moiety B (e.g., x is 2-10, or x is 2-4, or x is 3), and R$_a$ and R$_b$ can be, independently, hydrogen or an optional substituents such as a hydrocarbon such as an alkyl group such as methyl. For example, as described above, an alkyl group such as a $C_1$-$C_6$ alkyl group such as a methyl or ethyl can replace a hydrogen in the polyene. The substituent can be a hydrocarbon comprising only carbon and hydrogen and being free of a heteroatom such as oxygen or nitrogen. In another example, and alkoxy group such as methoxy or ethoxy can replace hydrogen. The double bonds of moieties (CHR$_a$═CHR$_b$) can be a mixture of cis and trans, or can be all trans.

In one embodiment, the bivalent polyene moiety B has two to ten double bonds. In another embodiment, the bivalent polyene moiety B has two to four double bonds. In one embodiment, the bivalent polyene moiety B has three double bonds which can be three conjugated double bonds.

In one embodiment, the double bonds of bivalent polyene moiety B are in an all trans configuration.

In one embodiment, the bivalent polyene moiety B is a $C_7$ hydrocarbon moiety with one methyl substituent and no heteroatoms represented by:

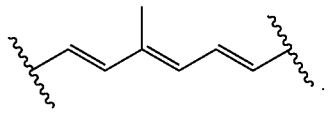

For monovalent moiety A, six-membered carbon rings are known in the art, whether saturated or unsaturated, including phenyl, cyclohexane cyclohexadiene, and cyclohexene rings. More particularly, the ionone moiety with a single cyclohexene ring is particularly known in the carotenoid art. In one embodiment, the monovalent moiety A consists of only one cyclohexene ring. The cyclohexene ring can be of the β or ε ring types as known in the carotenoid art, as shown below:

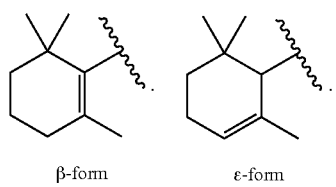

β-form      ε-form

In another embodiment, the cyclohexene ring of monovalent moiety A has a double bond in conjugation with a double bond of the polyene moiety B. In another embodiment, the monovalent moiety A is a $C_6$-$C_{12}$ moiety. In another embodiment, the monovalent moiety A is a $C_9$ moiety.

In other embodiments, for the monovalent moiety A, the substituent is a hydroxyl, ketone, epoxy, alkoxy, or polyether moiety. In another embodiment, the substituent is a hydroxyl moiety.

In one embodiment, the compound is represented by:

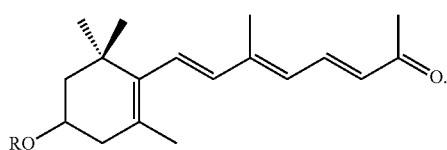

wherein RO— is the substituent and R can be, for example, hydrogen (RO— is hydroxyl substituent), an alkyl group such as a $C_1$-$C_{12}$ alkyl group (RO— is alkoxy substituent), or a monovalent group comprising ether moiety such as RO—R— or RO—RO—R— wherein R is a monovalent $C_1$-$C_{12}$ alkyl group or a bivalent $C_1$-$C_{12}$ alkylene group (RO— is a polyether substituent).

In one embodiment, the monovalent moiety A can be represented by formula X:

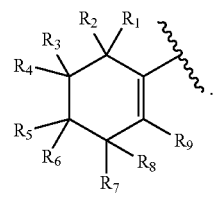

In another embodiment, the monovalent moiety A can be represented by formula XX:

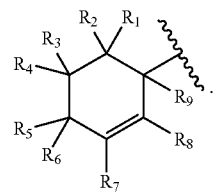

In formulae X and XX, $R_1$ and $R_2$ independently can be, for example, hydrogen or an alkyl group such as a $C_1$-$C_6$ alkyl group, or a $C_1$-$C_3$ alkyl group, including methyl. In one embodiment, $R_1$ and $R_2$ are each methyl.

In formulae X and XX, $R_3$ and $R_4$ independently can be, for example, hydrogen or an alkyl group such as a $C_1$-$C_6$ alkyl group, or a $C_1$-$C_3$ alkyl group, including methyl. In one embodiment, $R_3$ and $R_4$ are each hydrogen. Alternatively $R_3$ and $R_4$ can be a ketone group, or a group comprising oxygen.

In formulae X and XX, $R_5$ and $R_6$ independently can be, for example, hydrogen, a monovalent moiety comprising oxygen such as hydroxyl or carboxyl, or an alkyl group such as a $C_1$-$C_6$ alkyl group, or a $C_1$-$C_3$ alkyl group, including methyl. In one embodiment, $R_5$ is hydroxyl and $R_6$ is hydrogen. In one embodiment, the stereochemistry for $R_5$ and $R_6$ and the cyclohexane ring can be represented by:

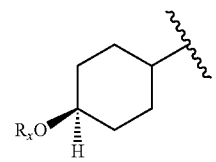

wherein $R_5$ is $R_xO$— and $R_6$ is hydrogen, and $R_x$ can be hydrogen.

In one embodiment, the monovalent moiety A is represented by:

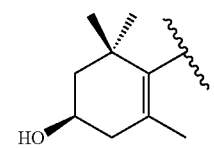

In formulae X and XX, $R_7$, $R_8$, and $R_9$ independently can be, for example, hydrogen or an alkyl group such as a $C_1$-$C_6$ alkyl group, or a $C_1$-$C_3$ alkyl group, including methyl. In one embodiment, for formula X, $R_7$ and $R_8$ are hydrogen and $R_9$ is methyl.

In other embodiments, the monovalent moiety A can comprise one or more ring carbonyl moieties as shown for example in the following structure:

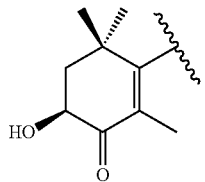

In one embodiment, for formula X, $R_7$ and $R_8$ are present as a ketone and $R_9$ is methyl.

In other embodiments, the monovalent moiety A can comprise one or more ring epoxy moieties as shown for example in the following structure, having a cyclohexane ring:

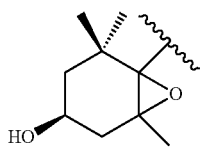

or, showing a stereochemical configuration for the epoxy group:

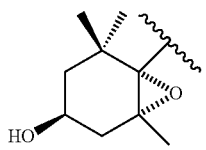

In one embodiment, the monovalent moiety C linked to B by a carbonyl moiety is represented by —C(O)—R, wherein R is an alkyl group or a carboxylic acid group.

In one embodiment, the monovalent moiety C linked to B by a carbonyl moiety is represented by —C(O)—R, wherein R is a methyl group.

In one embodiment, C is represented by:

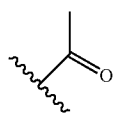

The combinations of A, B, and C as described herein can include all combinations of A, B, and C which man or nature can synthesize.

One particular embodiment can be represented by:

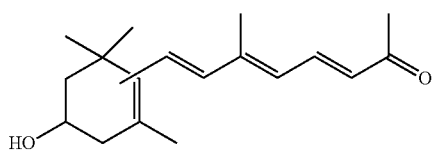

Another particular embodiment can be represented by:

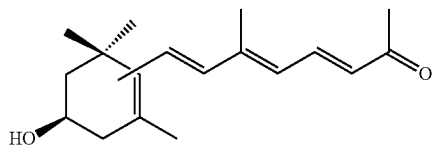

In one embodiment, the bivalent polyene moiety B has two to ten double bonds, and wherein the monovalent moiety A comprises a cyclohexene ring, and the cyclohexene ring has a double bond in conjugation with a double bond of the polyene moiety B, and wherein the monovalent moiety C linked to B by a carbonyl moiety is represented by —C(O)—R, wherein R is an alkyl group.

In another embodiment, the bivalent polyene moiety B has two to four double bonds, and wherein the monovalent moiety A is a $C_6$-$C_{12}$ moiety, and wherein the monovalent moiety C linked to B by a carbonyl moiety is represented by —C(O)—R, wherein R is an alkyl group, wherein R is methyl.

In other embodiments, the compound which is represented by A-B-C can be represented by structure Z:

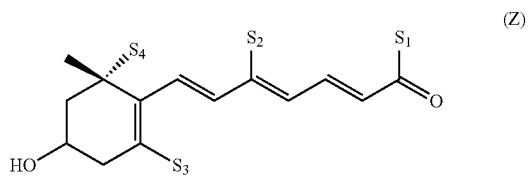

wherein $S_1$ can be an alkyl or a carboxylic acid group; wherein $S_2$ can be an alkyl, carboxylic acid, or —CH$_2$OH group; wherein $S_3$ can be an alkyl, a carboxylic acid, or a —CH$_2$OH group; and wherein $S_4$ can be an alkyl, carboxylic acid, or —CH$_2$OH group. In one embodiment, $S_1$, $S_2$, $S_3$, and $S_4$ are methyl. In another embodiment, $S_1$, $S_2$, $S_3$, and $S_4$ are not methyl. In structure Z, the —OH moiety stereochemically can be above or below the cyclohexene ring.

In other embodiments, the compound represented by one of the following structures (I)-(VIII):

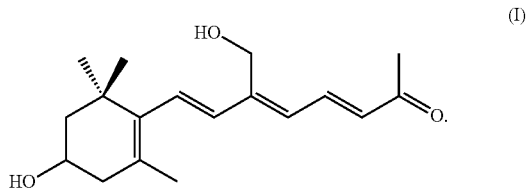

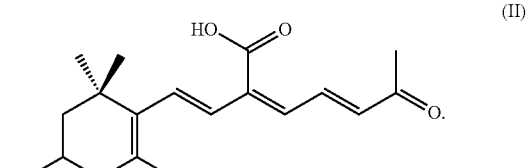

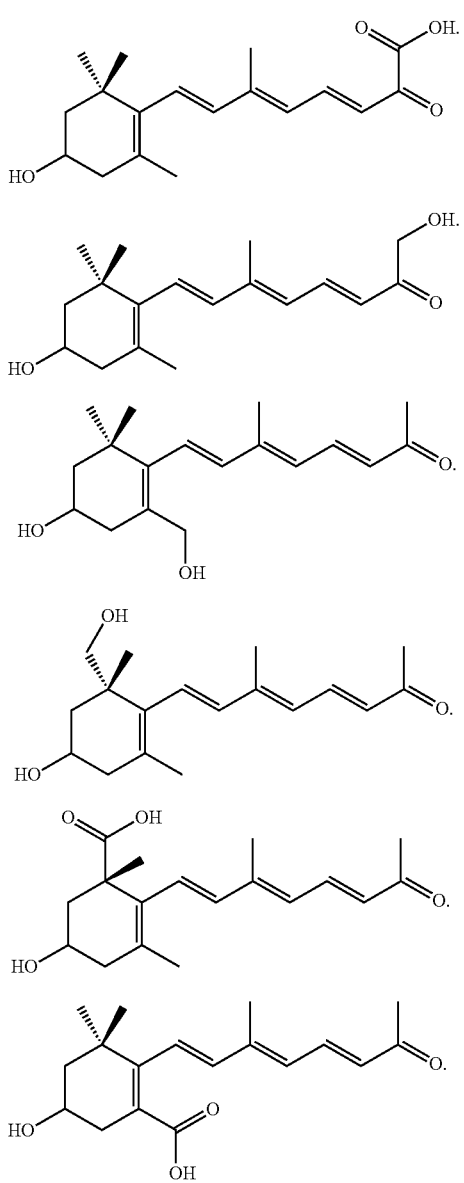

In another embodiment, the compound is 3-OH-β-apo-13-carotenone.

Method of Making Compound

The inventive compounds can be isolated from nature or made synthetically. Methods known in the art can be used to isolate the compound from natural sources. Preparation methods are included in, for example, US Patent Publication 2009/0264681.

Composition

The inventive compounds can be used alone or also used combined with one or more other ingredients to form compositions or formulations. For example, the composition can be adapted for a particular delivery mechanism. Additional additives, active compounds, and solvents can be used as appropriate for a particular application and delivery rate. The compositions can comprise, consist essentially of, or consist of the active compound for plant growth regulation along with one or more other compounds or materials.

Formulating plant growth regulators or promoters is known in the art. See, for example, U.S. Pat. No. 5,837,653; US Patent Publications 2015/0087508 and 2015/0011392.

Known types of adjuvants can be used including, for example, one or more carriers, solvents or surface active agents. These can be agriculturally acceptable formulation adjuvants.

Formulations can include, for example, dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, capsule suspensions (CS) and seed treatment formulations. The formulation type chosen in any instance will depend upon the particular purpose envisaged and the physical, chemical and biological properties of the active compound. See, for example, *Manual on Development and Use of FAO Specifications for Plant Protection Products,* 5th Edition, 1999.

In addition, the compositions can be liquids, solutions, emulsions, and the like. If emulsions are used, particles can be present characterized by an average particle size. The active compound can be dispersed in the particle, and the particle can include, for example, polymers. Encapsulation methods can be used.

For example, in one embodiment, the compound is a first compound, and the composition further comprises at least one second compound different from the first and which also is a plant growth regulator (PGR). The relative molar or weight amounts of the two components can be adapted to find effective amounts and synergistic effects. In one case, the first compound may be present in a higher molar or weight amount compared to the second, whereas in another case the first compound may be present in a lower molar or weight amount compared to the second. In some, cases, the two compounds may be present is substantially equal molar or weight amounts. More particularly the molar or weight ratio for first and second compounds can be, for example, from 9:1 to 1:9, or 8:1 to 1:8, or 7:1 to 1:7, or 6:1 to 1:6, or 5:1 to 1:5, or 4:1 to 1:4, or 3:1 to 1:3, or 2:1 to 1:2, or 1.5:1 to 1:1.5, or 1.2:1 to 1:1.2, or about 1:1.

Examples of plant growth regulators which can be formulated into the composition include, for example, auxins, cytokinins (CKs), gibberellins (GBs), abscisic acid (ABA), and ethylene.

Other plant growth regulators include, for example, brassinosteroids, salicylic acid, jasmonates, plant peptide hormones, polyamines, nitric oxide (NO), strigolactones, and karrikins.

In one embodiment, the compound is a first compound, and the composition further comprises at least one second compound different from the first which also is a plant growth regulator, wherein the second compound is, for example, auxin, cytokinin, gibberlin, or ethylene.

In one embodiment, the compound is a first compound, and the composition further comprises at least one second compound different from the first which also is a plant growth regulator, wherein the second compound is auxin.

In one embodiment, the composition is in the form of a liquid at 25° C.

In one embodiment, the composition further comprises at least one solvent or at least one solvent system including an aqueous solvent system. In one embodiment, the composition further comprises water.

In one embodiment, water is the only solvent used. The solvent composition can be formulated for a particular application. For example, concentrations can be varied, co-solvents can be used, and additives can be included.

Effective Amount of Composition and Compound

One skilled in the art can adapt the amount of the composition used for a particular application. In addition, one skilled in the art can adapt the amount of the compound used in the composition for a particular application. These amounts can be called "plant growth regulating amounts." The amounts can be, more specifically, effective for a particular example of plant growth such as root promotion or seed germination.

The effective concentration of the compound in the composition can be in the nanomolar or micromolar range. In one embodiment, the effective concentration of compound in the composition is in the range of, for example, 0.01 µM to 50 µM, or 0.01 µM to 25 µM, or 0.5 µM to 50 µM, or 0.1 µM to 10 µM, or 0.5 µM to 2.5 µM. Alternatively, the compound can be in a concentration of 0.01 ppm to 100 ppm, or 0.1 ppm to 10 ppm. The composition can be used in effective amounts and can be applied at effective rates. The frequency of the treatment can be adapted for effective treatment. Single or multiple treatments can be carried out.

The rest of the composition can be the adjuvant(s) such as carrier(s), solvent(s), and surface active agent(s).

Plants

A wide variety of plants can be used in the inventive methods herein described including a wide variety of monocots and dicots. The classes, subclasses, orders, families, genus, species, and varieties are not particularly limited. In particular, any plant which has a root system can be the subject of the root promotion described herein. The type of root system present is not particularly limited. The age of the plant is not particularly limited, but the plant can be in a younger form such as a seedling.

Cereal grains and related plants, including various rices, can be used including long, medium, and short grained rices. *Arabidopsis* plants and related plants can be used. Sugar cane, maize, pepper, and tomato can be used. The compositions can be used on particular strains of these and other plants in the plant kingdom including different parts of the plants.

Effects and Results of Method of Use

The compounds described herein can have a variety of effects and results when used as described herein. For example, they can determine the formation of flowers, early flowering, stems, leaves, the shedding of leaves, and the development and ripening of fruit. In addition, they can shape the plant, affecting seed growth, time of flowering, the sex of flowers, senescence of leaves, and fruits. They also, for example, can affect which tissues grow upward and which grow downward, leaf formation and stem growth, fruit development and ripening, plant longevity, and even plant death.

The compounds, compositions, and methods can be used in such methods as plant propagation including cutting, grafting, micropropagation, and tissue culture methods. The compounds and compositions can be used as a rooting compound.

The compounds, compositions, and methods can be used to impact seed germination and dormancy.

One embodiment also is a plant propagation material treated with a composition as described herein. "Plant propagation material" can be, for example, any and all the generative parts of the plant, such as seeds, which can be used for the multiplication of the latter and vegetative plant materials such as cuttings and tubers. In particular, there may be mentioned the seeds, roots, fruits, tubers, bulbs, and rhizomes.

Methods for applying active ingredients to plant propagation material, especially seeds, are known in the art, and include, for example, spraying, dressing, coating, pelleting and soaking application methods of the propagation material. The treatment can be applied to the seed at any time between harvest of the seed and sowing of the seed or during the sowing process. The seed may also be primed either before or after the treatment. The compound or compositions as described herein may optionally be applied in combination with a controlled release coating or technology so that the compound is released over time.

The composition of the present invention may be applied pre-emergence or post-emergence. Suitably, where the composition is being used to regulate the growth of crop plants, it may be applied pre or post-emergence, but preferably post-emergence of the crop. Where the composition is used to promote the germination of seeds, it may be applied pre-emergence. The composition can be applied to leaves.

Exclusionary Embodiments

In some embodiments for the types of compounds, the compound 3-OH-β-apo-13-carotenone can be excluded from a larger listing of compounds. For example, this compound can be excluded from embodiments for a composition, or embodiments for a method, or embodiments for a listing of compounds.

WORKING EXAMPLES

Further embodiments are provided in the non-limiting working examples described below.

Figure 1:
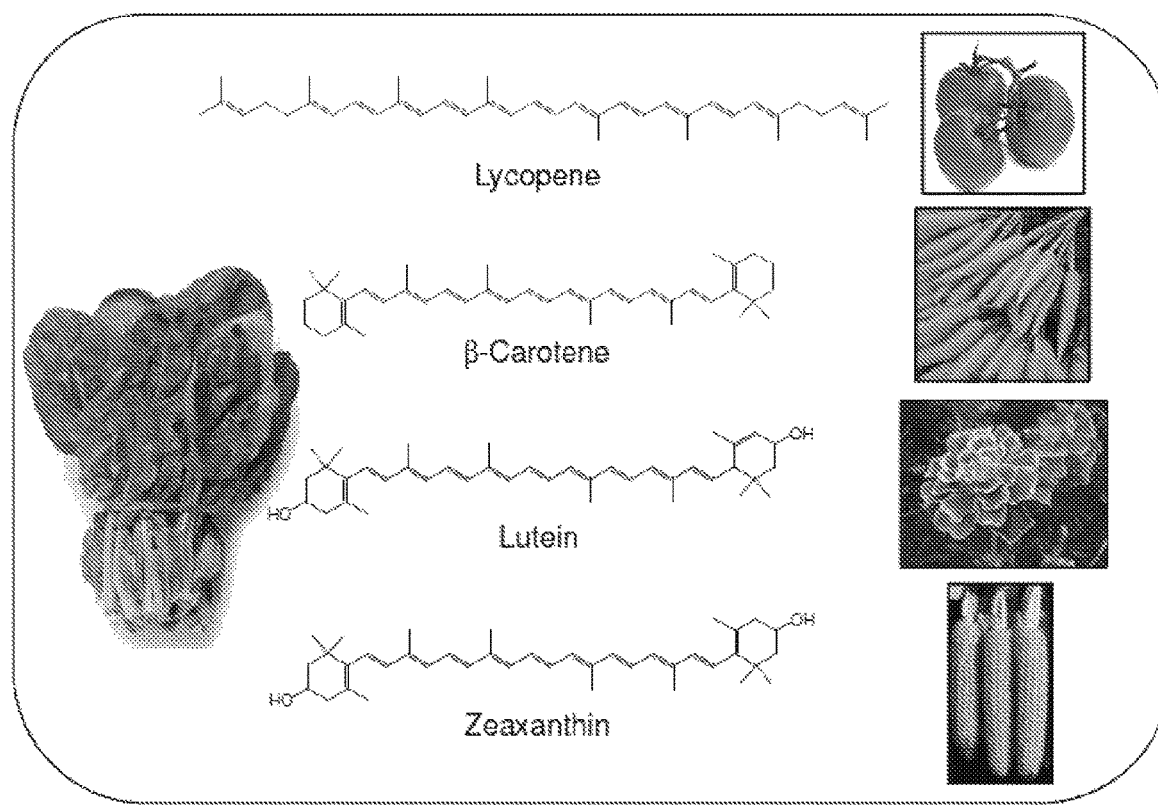
FIG. 1: Examples of carotenoids. Carotenoids derive from the same pathway that starts with a colorless compound (phytoene, not shown). Green tissues (left side) accumulate different carotenoids, with lutein followed by β-carotene as the major representatives. Fruits and flowers and other plant tissues may contain other carotenoids as major representatives. Examples are Lycopene in tomato fruits, β-carotene in carrots, lutein in marigold flowers, and zeaxanthin in corn.
Figure 2:
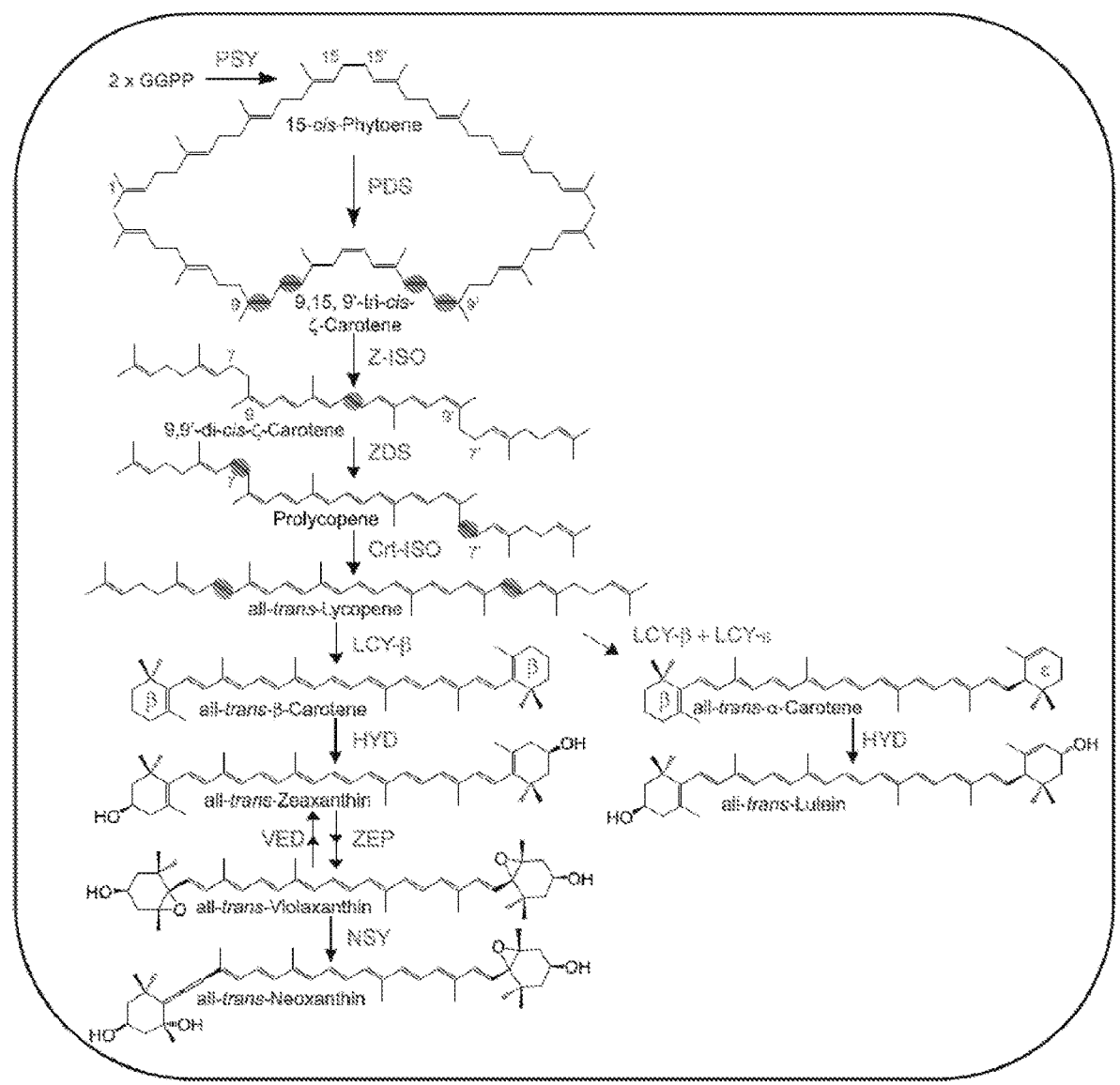
FIG. 2: Plant carotenoid biosynthesis. Phytoene synthase (PSY) catalyzes the condensation of two geranylgeranyl diphosphate (GGPP; C20) molecules to 15-cis-phytoene, which is then converted by phytoene desaturase (PDS), ζ-carotene isomerase (Z-ISO), ζ-carotene desaturase (ZDS), and carotene isomerase (Crt-ISO) into all-trans-lycopene via different. all-trans-Lycopene is the precursor of the cyclic carotenoids all-trans-β-carotene and all-trans-α-carotene, which are formed by lycopene-β-cyclase (LCY-β) and the combined activity of LCY-β and lycopene-ε-cyclase (LCY-ε), respectively. Lutein and zeaxanthin are produced by hydroxylases (HYD) from -α-carotene and β-carotene, respectively. all-trans-Zeaxanthin can be reversibly epoxidized to violaxanthin, the precursor of neoxanthin. Epoxidation and de-epoxidation are catalyzed by zeaxanthin epoxidase (ZEP) and violaxanthin de-epoxidase (VDE), and all-trans-neoxanthin is produced by neoxanthin synthase (NSY).
Figure 3:
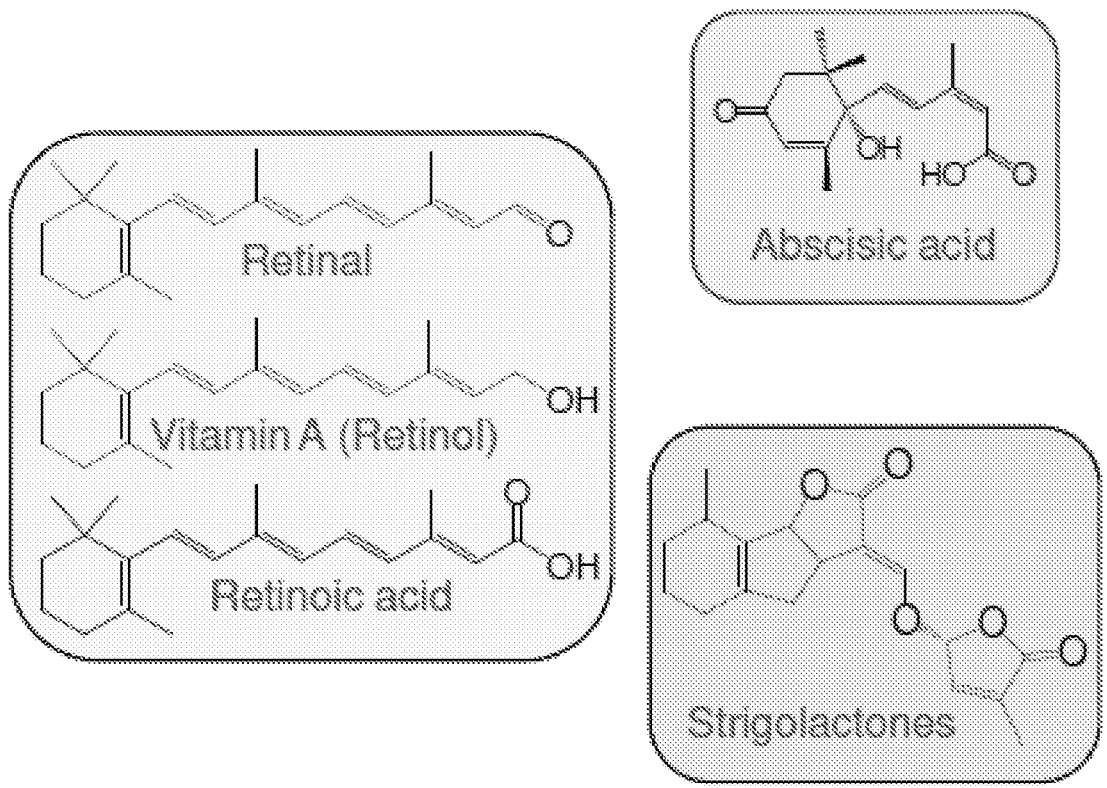
FIG. 3: Examples of carotenoid-derived bioactive compounds. The best known carotenoid-derived compounds are the retinoids, which include the vision chromphore retinal, vitamin A and vertebrate morphogen retinoic acid. The plant hormones abscisic acid (ABA) and strigolactones (SLs) derive also from carotenoids. ABA regulates the stress response of plants to drought and other unfavorable conditions and is responsible for seed dormancy. SLs. regulate plant architecture and are involved in the communication of plants with the soil-living environment.
Figure 4:
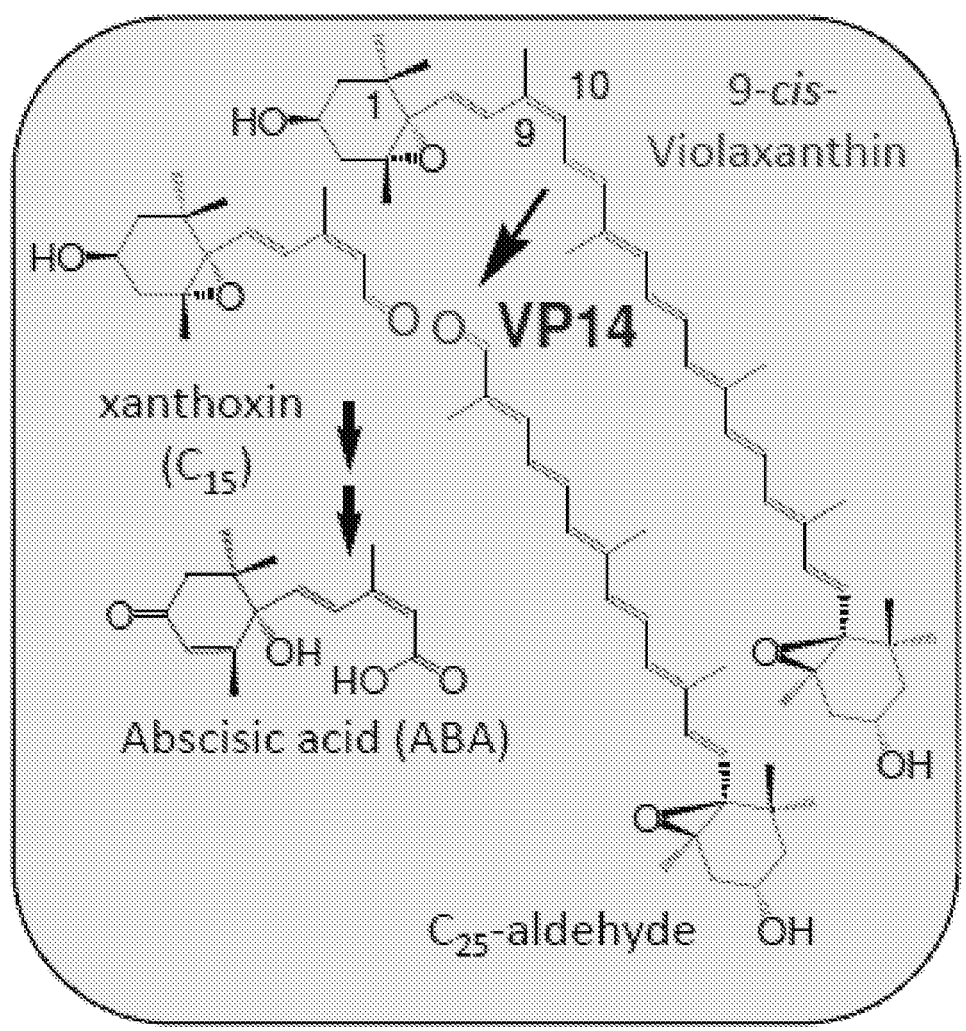
FIG. 4: ABA biosynthesis. ABA arise by oxidative cleavage of cis-configured epoxy-carotenoids, such as 9-cis-violaxantin. The reaction leads to the precursor xanthoxin and is catalyzed by 9-cis-epoxy-carotenoids cleavage dioxygenases (NCEDs) such as the maize VP14.
Figure 5:
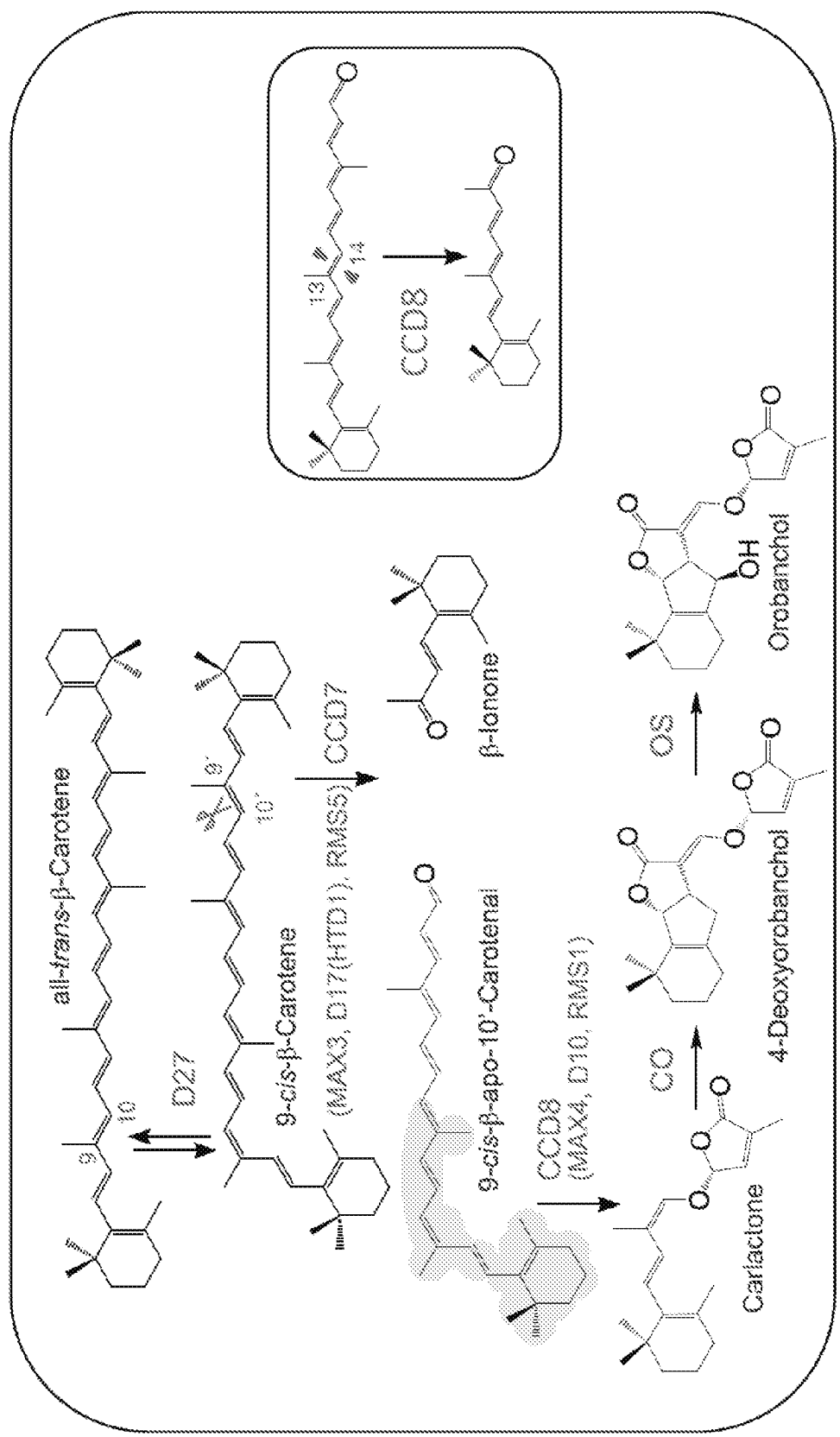
FIG. 5: Strigolactone Biosynthesis. The enzyme DWARF27 (D27) catalyzes the 9-cis/all-trans isomerization of β-carotene. The carotenoid cleavage dioxygenase 7 (CCD7) then mediates the stereospecific cleavage of 9-cis-β-carotene at the C9'-C10' double bond, yielding the intermediate 9-cis-β-apo-10'-carotenal and β-ionone. In one step, CCD8 converts 9-cis-β-apo-10'-carotenal into the SL carlactone and an unidentified second product. Carlactone is thought to derive from the shaded part of the precursor 9-cis-apo-10'-carotenal. The rice enzyme carlactone oxidase (CO) Os900 catalyzes repeated oxygenation and ring closures to form 4-deoxyorobanchol (ent-2'-epi-5-deoxystrigol). The rice orobanchol synthase (OS, formerly designated as ent-2'-epi-5-deoxystrigol-4-hydroxylase) converts 4-deoxyorobanchol to orobanchol. Inset: CCD8 enzymes also cleave all-trans-b-apo-10'-carotenal. However, this reaction yields a "classical" cleavage product: b-apo-13-carotenone also called d'orenone.
Figure 6:
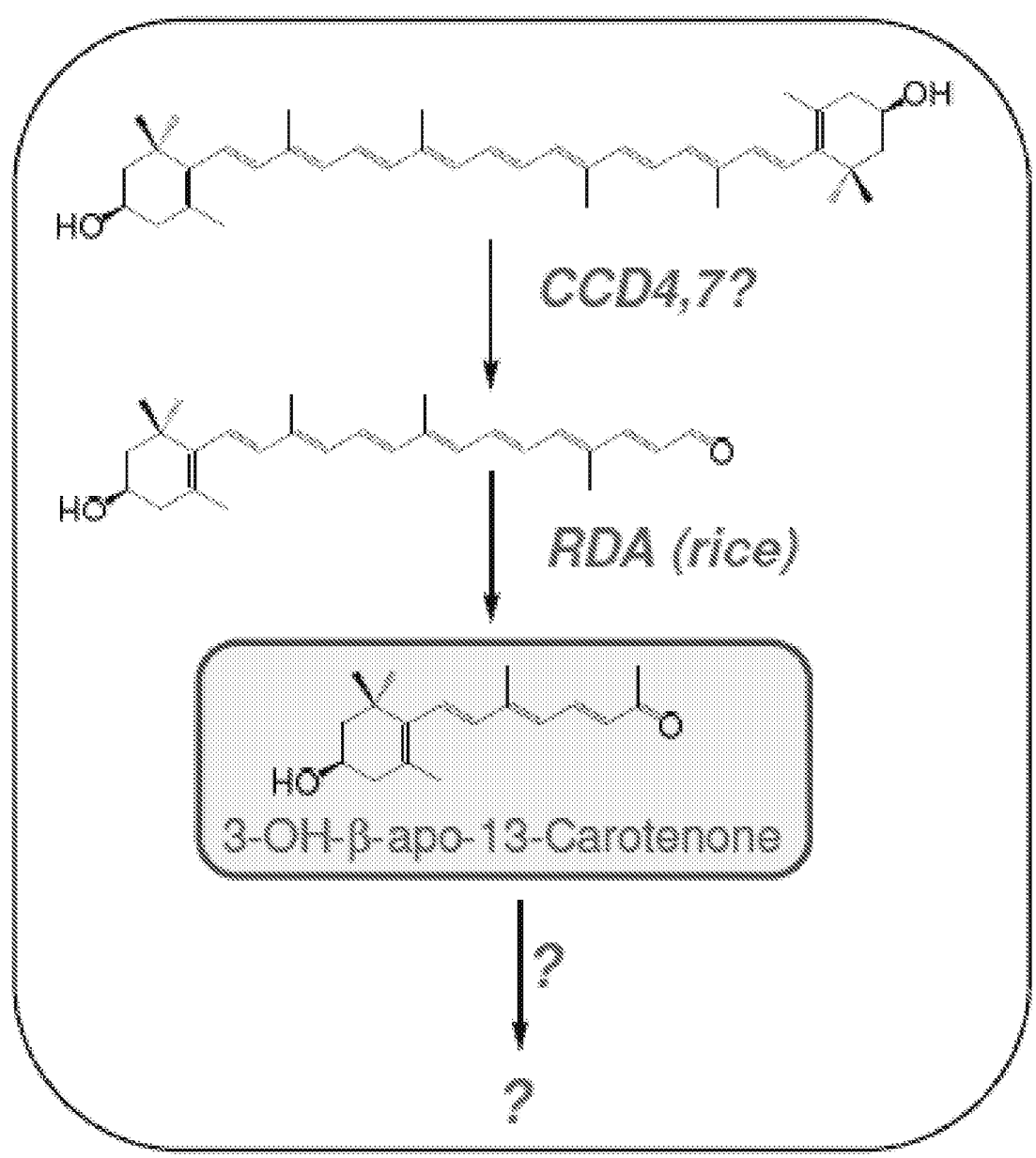
FIG. 6: The rice enzyme RDA forms 3-OH-β-apo-13-Carotenone in vitro. In vitro incubation of heterogously expressed RDA (a rice carotenoid cleavage dioxygenase) with all-trans-3-OH-β-apo-10'-carotenal leads to all-trans-3-OH-β-apo-13-carotenone. The nature of the product was confirmed by comparison to a synthetic, authentic standard, using HPLC and LC-MS. It is possible that all-trans-3-OH-β-apo-10'-carotenal is not a final product but an intermediate of a metabolic pathway.

In the course of work on CCDs from rice, the activity of the Os09g0321200 encoded enzyme to which one can refer to as RDA was investigated (the rice strigolactone biosynthetic enzyme CCD8b encoded by Os01g0746400 shows around 39% homology to RDA at the amino acid level). Like CCD8 (see FIG. 5, inset, and brief description of FIG. 5), RDA does not cleave intact carotenoids, but apocarotenoids that can be produced either by the activity of other carotenoid cleavage dioxygenases or non-enzymatically, i.e. by reactive oxygen species (13). In vitro, the enzyme showed wider substrate specificity with respect to all-trans-configured apocarotenoids. The best activity was observed with 3-OH-β-apo-10'-carotenal, a substrate that was converted by the enzyme into 3-OH-β-apo-13-carotenone (FIG. 6), a compound that has not been described as a plant CCD product or metabolite. However, 3-OH-β-apo-13-carotenone is similar to d'orenone (β-apo-13-carotenone), a compound that was shown to block tip growth of root hairs, however at high concentration (16) and which can be produced by CCD8 enzymes in vitro (1). It should be mentioned that d'orenone (3-apo-13-carotenone) presence in planta has also not been confirmed yet.

Figure 7:
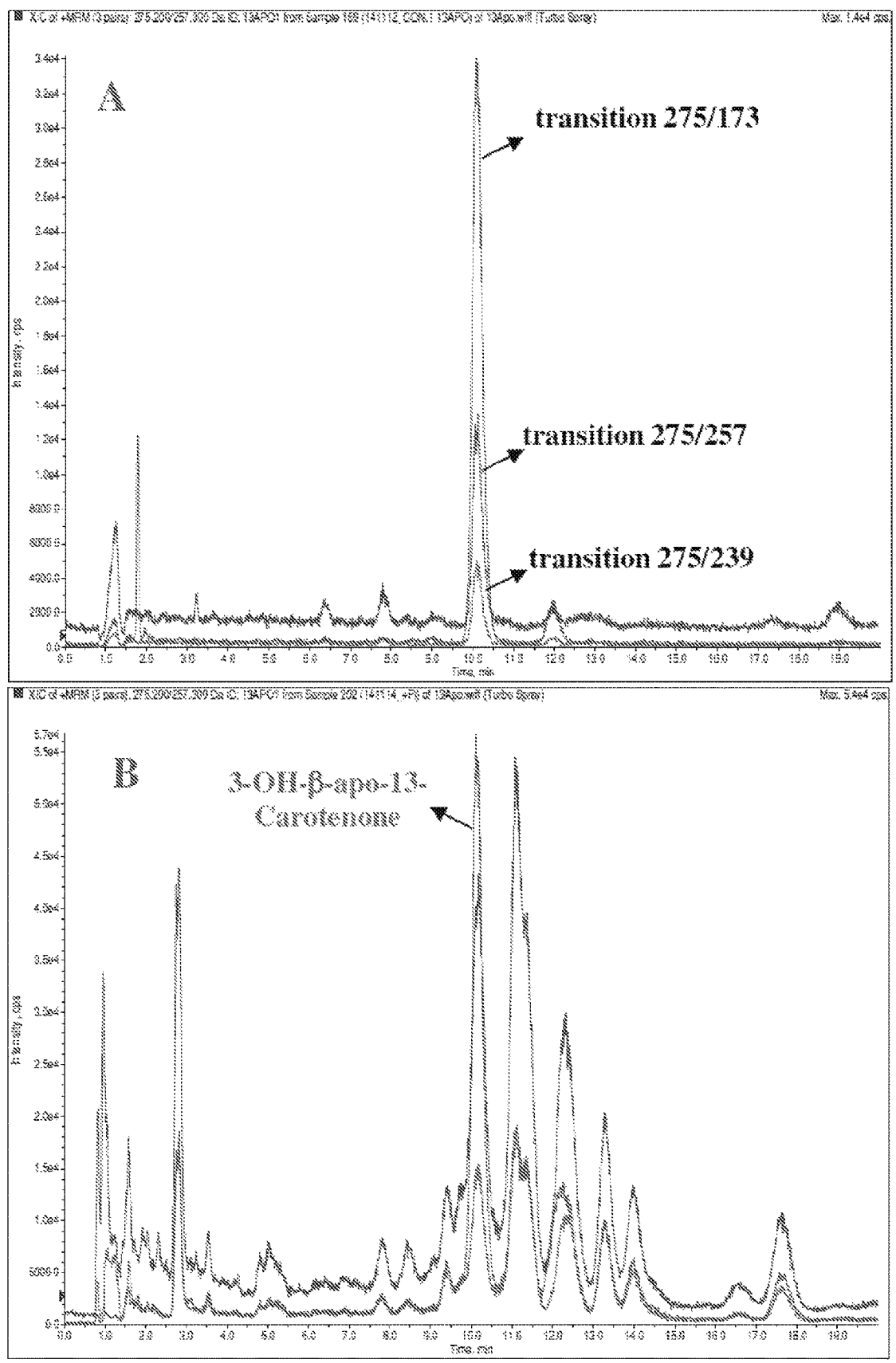
FIG. 7: 3-OH-β-apo-13-Carotenone is a natural metabolite (I). A: Using a synthetic standard, we optimized HPLC separation and LC-MS detection of 3-OH-β-apo-13-Carotenone. The detection was performed by multiple reaction monitoring (MRM) using the selected transition 275/173, 275/257 and 275/239. B: The same signals corresponding to 3-OH-β-apo-13-Carotenone were detected in total rice roots extract.
Figure 8:
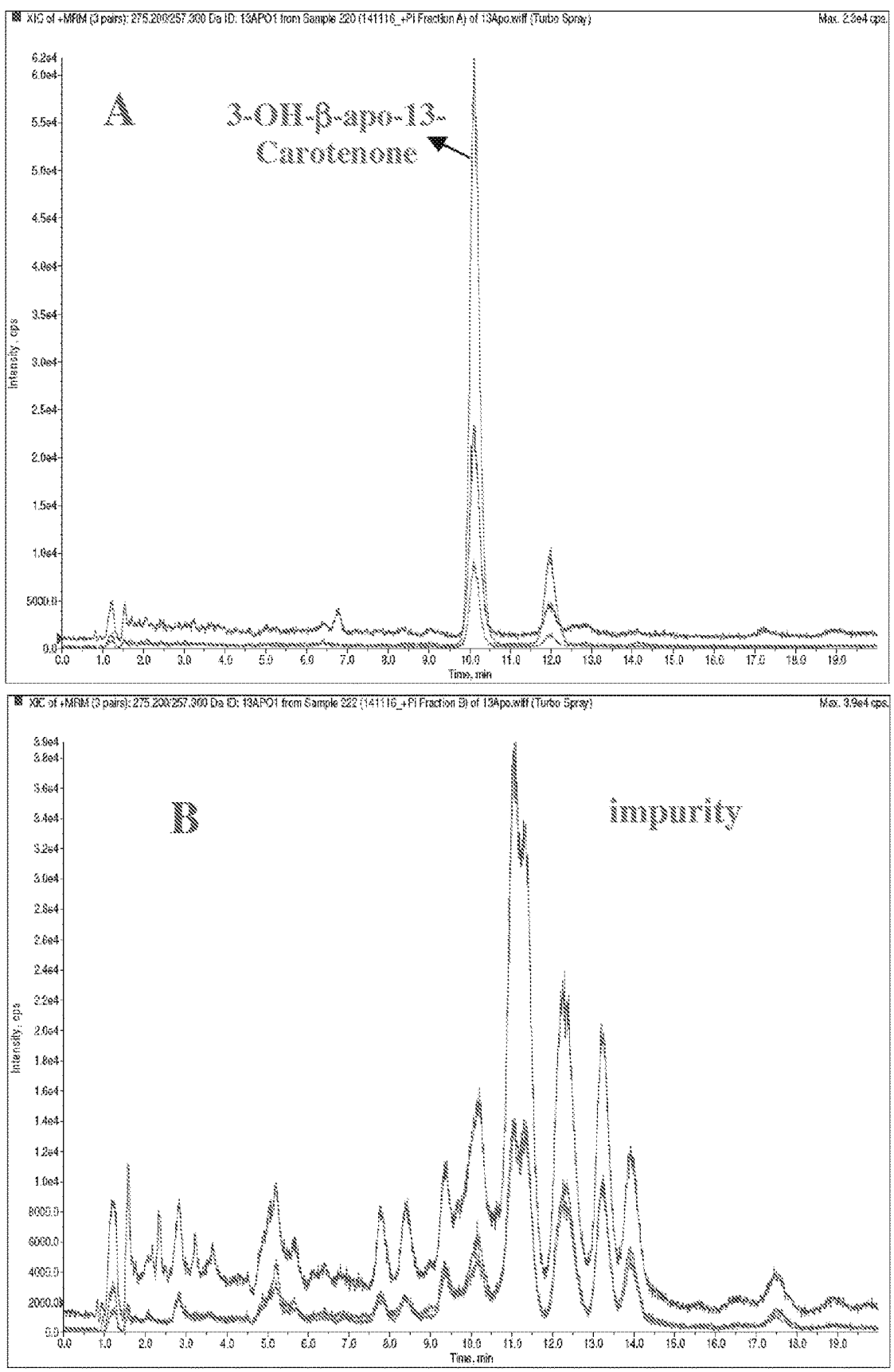
FIG. 8: 3-OH-β-apo-13-Carotenone is a natural metabolite (II). To obtain a more clear and enriched signal, total rice roots extract was fractioned using a Silica SPE column. Fraction A (A) eluted with hexane/ethyl acetate 10:90 showed a clear 3-OH-β-apo-13-Carotenone signal that was absent in fraction B (B) that contained the impurities and was obtained by methanol/ethyl acetate 10:90 as a second eluent.

To confirm that 3-OH-β-apo-13-carotenone is a natural plant metabolite, a Multiple Reaction Monitoring (MRM)-based LC-MS protocol was established (FIG. 7). Using this protocol, it was demonstrated that 3-OH-β-apo-13-carotenone is a natural plant metabolite occurring in rice roots (FIG. 8), but also in rice shoots and in *Arabidopsis* (not shown). Using deuterium-labeled standard, the amounts of this compound in rice and *Arabidopsis* were also determined. The results showed that 3-OH-3-apo-13-carotenone occurs in tens to hundreds of nano-grams per gram lyophilized plant material, depending on the tissue and plant species.

Figure 9:
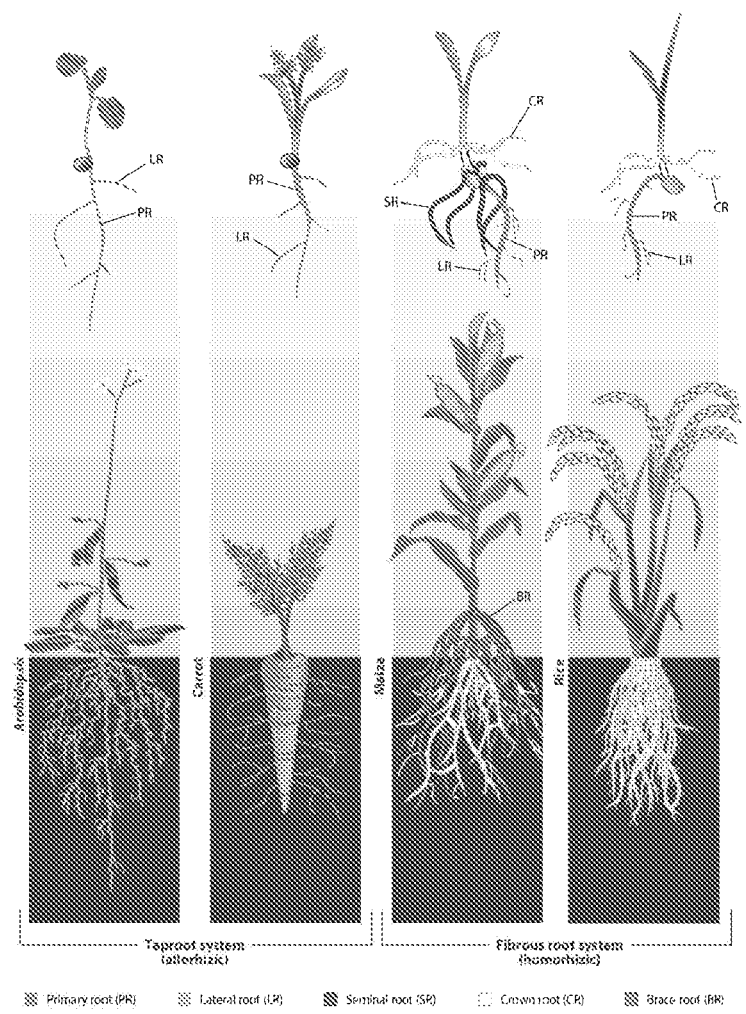
FIG. 9: Schematic representation of typical root systems found in most dicotyledons and monocotyledons.

Roots are the plant organ responsible for anchorage and uptake of water and nutrients. Therefore, root architecture is a major component in determining plant fitness, and crop performance and yield (14). Plant roots originate from the radical that is already established during embryogenesis and which grows to the primary root (PR). Gymnosperms and dicotyledons have a so called allorhizic root system in which the primary root builds a thick central root—called taproot- and develops lateral roots (LRs). Usually, the taproot is maintained during the whole life cycle, in contrast to monocotyledons where the root system derived from the PR is short-lived, and only important in seedlings. Root functions are then exerted by a different root system, fibrous root system or homorhizic system, that from shoot-born roots, also called adventitious roots (ARs) (21). ARs always originate post-embryonically from tissues other than primary root, i.e. shoots, stems, or leaves. In wheat, rice and other cereals, the postembryonic shoot-born roots are called crown roots (CRs) or, in the case of maize, brace roots (5) (FIG. 9).

ARs also naturally develop in many dicotyledonous species, such as strawberries, which propagate vegetatively, and can be induced, in both monocotyledons and dicotyledons, either by certain environmental changes, such as flooding and dark-light transitions, or by and/or hormone application. The ability of cuttings and explants to develop ARs is exploited in horticulture and forestry for mass production of cloned plants (for review, see (5)).

Plants modify the architecture of their roots depending on the growth conditions and nutrients and water availability. Under phosphate deficiency, plants increase the root-to-shoot ratio and, in many cases, develop a shallower root system with shorter primary roots, denser root hairs, and more and longer lateral roots. This root architecture provides better access to phosphate, which usually accumulates in the upper part of the soil, a strategy designated as "topsoil foraging" (12; 14), while deeper roots improve growth under drought conditions (14).

Expression analysis of the rice gene Os09g0321200 (RDA) showed relatively high transcript levels in roots. Therefore, it was tested whether the RDA-enzymatic product 3-OH-β-apo-13-carotenone is present in this tissue. Using LC-MS analysis, it was confirmed that 3-OH-β-apo-13-carotenone is a natural metabolite that occurs in rice roots, but also in green tissues. We also detected this compound in *Arabidopsis* roots and shoots.

Figure 10A:
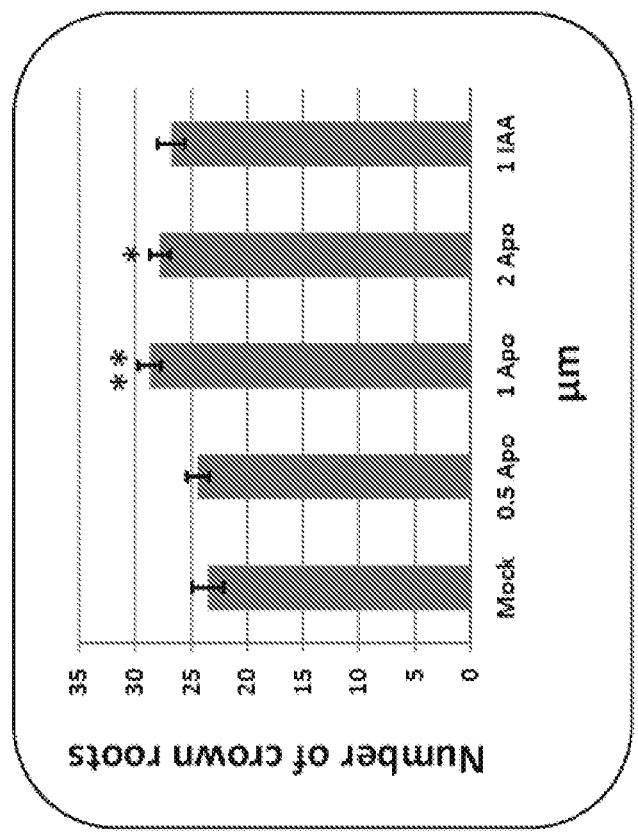
(FIG. 10A) Number of crown roots of rice seedlings 2 weeks after treatment. Each value represents the mean of 10 seedlings. Error bar indicates standard error. Asterisks denote a significant difference from the mock treatment by student t-test (* P<0.05; ** P<0.01).
Figure 10B:
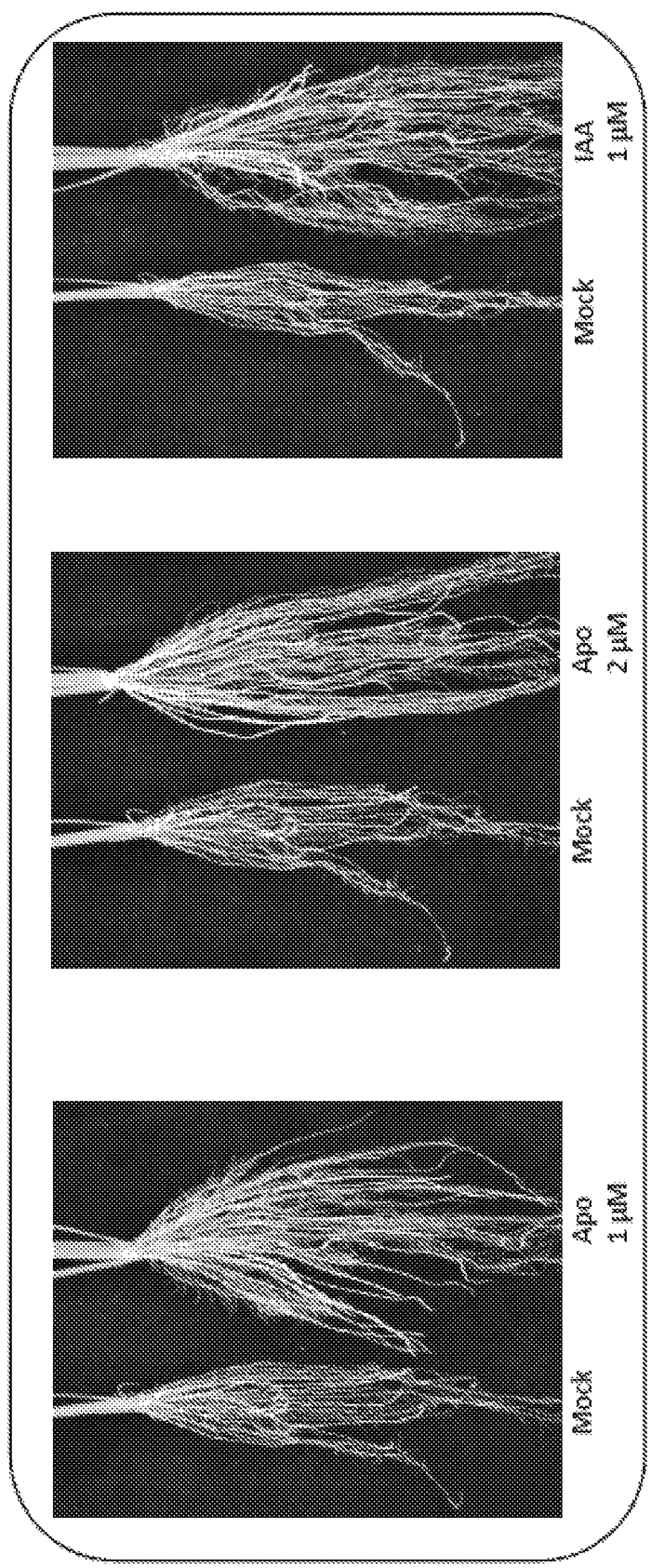
(FIG. 10B) Photographs of roots of rice seedlings 2 weeks after treatment. Note the increased number of crown roots in the 3-OH-β-apo-13-Carotenone (Apo) treated samples.

Based on the possibility that 3-OH-β-apo-13-carotenone may have a role in plant development, the impact of this compound on rice roots was investigated. For this purpose, rice seedling were grown hydroponically and treated with different concentrations of this compound. As shown in FIGS. 10A and 10B, the treatment with the compound led to an obvious increase in the number of crown roots at micromolar concentrations. This increase resulted in around 30% increase in root and shoot biomass (FIG. 11).

Dicotyledonous plants do not develop crown roots but can produce adventitious roots that, originate from stems, similar to the crown roots, or from other non-root tissues. Therefore, we tested whether β-apo-13-carotenone can also induce adventitious root formation in the model plant *Arabidopsis thaliana*. As shown in FIGS. 12A and 12B, the compound exerted a clear induction on the number of hypocotyl-derived adventitious roots that usually arise spontaneously after dark-light transition. Highest activity—around 50% increase, was obtained with 2.5 µM concentrations (FIGS. 12A and 12B). Similar results were obtained with wounding induced hypocotyl-derived adventitious roots (not shown). Moreover, treatment with 3-OH-β-apo-13-carotenone led to a noticeable increase (duplication) in the number of leaf-derived adventitious roots (FIG. 13). In addition, treatment with the compound with 2.5 µM of the compound clearly increased the number of lateral roots (FIG. 14).

To ensure that the biological activity observed is caused by 3-OH-β-apo-13-carotenone and not by a possible contamination with a different compound that may be included during the organic synthesis, HPLC was used to isolate highly pure 3-OH-β-apo-13-carotenone, and the purified compound was applied.

As shown in FIG. 14, an increase in lateral root number was detected similar to that observed before. This result clearly demonstrates that the growth promoting effects observed in these experiments are exerted by 3-OH-β-apo-13-carotenone.

Also investigated was possible effect of combining 3-OH-β-apo-13-carotenone with auxin. As shown in FIG. 15, simultaneous treatment with both compounds showed synergetic effects expressed by a duplication of the lateral root density, while single treatment with 3-OH-β-apo-13-carotenone and auxin caused only around 20% to 30% increase, respectively.

Also investigated was the effect of the compound on primary root length. A small but significant increase upon treatment with this compound was observed (FIG. 16).

The compound also in greenhouse experiments showed growth-promoting effects and early flowering.

CITED REFERENCES

1. Alder A, et al., 2008. Carotenoid oxygenases involved in plant branching catalyse a highly specific conserved apocarotenoid cleavage reaction. *The Biochemical journal* 416:289-96
2. Alder A, et al., 2012. The path from beta-carotene to carlactone, a strigolactone-like plant hormone. *Science* 335:1348-51
3. Auldridge M E, et al., 2006. Plant carotenoid cleavage oxygenases and their apocarotenoid products. *Current opinion in plant biology* 9:315-21
4. Avendano-Vazquez A O, et al., 2014. An Uncharacterized Apocarotenoid-Derived Signal Generated in zeta-Carotene Desaturase Mutants Regulates Leaf Development and the Expression of Chloroplast and Nuclear Genes in *Arabidopsis*. The Plant cell 26:2524-37
5. Bellini C, et al., 2014. Adventitious roots and lateral roots: similarities and differences. *Annual review of plant biology* 65:639-66
6. DellaPenna D, et al., 2006. Vitamin Synthesis in Plants: Tocopherols and Carotenoids. *Annu. Rev. Plant Biol.* 57:711-38
7. Frusciante S, et al., 2014. Novel carotenoid cleavage dioxygenase catalyzes the first dedicated step in saffron crocin biosynthesis. *Proceedings of the National Academy of Sciences of the United States of America* 111
8. Kachanovsky D E, et al., 2012. Epistasis in tomato color mutations involves regulation of phytoene synthase 1 expression by cis-carotenoids. *Proc Natl Acad Sci USA* 109:19021-6
9. Medina H R, et al., 2011. Cleavage oxygenases for the biosynthesis of trisporoids and other apocarotenoids in Phycomyces. *Molecular microbiology* 82:199-208

10. Moise A R, et al., 2014. Mechanistic aspects of carotenoid biosynthesis. *Chemical reviews* 114:164-93
11. Moise A R, et al., 2005. Related enzymes solve evolutionarily recurrent problems in the metabolism of carotenoids. *Trends in plant science* 10:178-86
12. Peret B, et al., 2011. Root developmental adaptation to phosphate starvation: better safe than sorry. *Trends in plant science* 16:442-50
13. Ramel F, et al., Triantaphylides C, Havaux M. 2012. Carotenoid oxidation products are stress signals that mediate gene responses to singlet oxygen in plants. *Proc Natl Acad Sci USA* 109:5535-40
14. Rogers E D, et al., 2014. Regulation of plant root system architecture: implications for crop advancement. *Current opinion in biotechnology* 32C:93-8
15. Scherzinger D, et al., 2010. The *Mycobacterium tuberculosis* ORF Rv0654 encodes a carotenoid oxygenase mediating central and excentric cleavage of conventional and aromatic carotenoids. *The FEBS journal* 277:4662-73
16. Schlicht M, et al., 2008. D'orenone blocks polarized tip growth of root hairs by interfering with the PIN2-mediated auxin transport network in the root apex. The Plant journal: for cell and molecular biology 55:709-17
17. Schwartz S H. 1997. Specific Oxidative Cleavage of Carotenoids by VP14 of Maize. *Science* 276:1872-4
18. Van Norman J M, et al., 2014. Periodic root branching in *Arabidopsis* requires synthesis of an uncharacterized carotenoid derivative. *Proc Natl Acad Sci USA* 111:E1300-9
19. Walter M H, et al., 2010. Apocarotenoids: hormones, mycorrhizal metabolites and aroma volatiles. *Planta* 232:1-17
20. Walter M H, et al., 2011. Carotenoids and their cleavage products: biosynthesis and functions. *Nat Prod Rep* 28:663-92
21. Pijut, P M, et al., 2011. Promotion of adventitious Root formation of Difficult-to-Root hardwood tree species. *Horticultural reviews* 38:213-251.

What is claimed:

1. A method of promoting plant growth comprising providing a plant or plant part with a composition comprising an effective amount of a compound, wherein the compound is 3-OH-β-apo-13-carotenone, wherein the compound increases lateral root growth in *Arabidopsis thaliana* at a concentration between 0.1 μM and 2.5 μM.

2. The method of claim 1, wherein the composition further comprises at least one compound selected from the group consisting of auxin, cytokinin, gibberellin, and ethylene.

3. The method of claim 1, wherein the composition further comprises at least one delivery compound which facilitates delivery of 3 OH-β-apo-13-carotenone.

4. The method of claim 2, wherein the composition comprises 3-OH-β-apo-13-carotenone and auxin.

5. The method of claim 1, wherein the plant is a monocotyledon or a dicotyledon.

6. The method of claim 1, wherein the plant is a gymnosperm.

7. The method of claim 1, wherein the plant is a cereal.

8. The method of claim 1, wherein the plant is selected from the group consisting of rice, sugar cane, maize, pepper and tomato.

9. The method of claim 5, wherein the plant belongs to the genus, *Arabidopsis*.

10. The method of claim 1, wherein the composition is a liquid at room temperature.

11. The method of claim 1, wherein the plant part is selected from the group consisting of seeds, plant cuttings, tubers, bulbs and rhizomes.

12. The method of claim 1, wherein the composition is applied to the plant post emergence of the plant.

13. The method of claim 1, wherein the composition is applied to plant seedlings.

* * * * *